US010329520B2

(12) United States Patent
Kang et al.

(10) Patent No.: US 10,329,520 B2
(45) Date of Patent: Jun. 25, 2019

(54) COMPOSITIONS AND METHODS FOR USE IN SURFACE DECONTAMINATION

(71) Applicant: Kinnos Inc., Brooklyn, NY (US)

(72) Inventors: Jason Kang, New York, NY (US); Kevin Tyan, New York, NY (US); Katherine Jin, New York, NY (US)

(73) Assignee: Kinnos Inc., Brooklyn, NY (US)

( * ) Notice: Subject to any disclaimer, the term of this patent is extended or adjusted under 35 U.S.C. 154(b) by 0 days.

(21) Appl. No.: 15/668,267

(22) Filed: Aug. 3, 2017

(65) Prior Publication Data

US 2017/0336373 A1 Nov. 23, 2017

Related U.S. Application Data

(63) Continuation of application No. 15/541,211, filed as application No. PCT/US2017/017509 on Feb. 10, 2017.

(Continued)

(51) Int. Cl.
| *A61L 2/22* | (2006.01) |
| *C11D 1/62* | (2006.01) |
| *C11D 3/44* | (2006.01) |
| *C11D 3/40* | (2006.01) |
| *G01N 31/22* | (2006.01) |
| *G01N 21/78* | (2006.01) |

(Continued)

(52) U.S. Cl.
CPC ............. *C11D 9/444* (2013.01); *A01N 59/00* (2013.01); *C11D 1/62* (2013.01); *C11D 3/044* (2013.01); *C11D 3/046* (2013.01); *C11D 3/3947* (2013.01); *C11D 3/40* (2013.01); *G01N 21/78* (2013.01); *G01N 31/226* (2013.01); *A61L 2/22* (2013.01); *C11D 3/3956* (2013.01)

(58) Field of Classification Search
None
See application file for complete search history.

(56) References Cited

U.S. PATENT DOCUMENTS 2,058,489 A * 10/1936 Murch ................ C09B 67/0077
8/524
3,609,075 A 9/1971 Barbera
(Continued)

FOREIGN PATENT DOCUMENTS

| CA | 2320536 A1 | 3/2001 |
| CN | 1817072 A | 8/2006 |

(Continued)

OTHER PUBLICATIONS

International Search Report dated Apr. 13, 2017 for International Application No. PCT/US2017/017509, filed Feb. 10, 2017, 3 pages.

*Primary Examiner* — Joseph D Anthony
(74) *Attorney, Agent, or Firm* — Muriel Liberto, Esq.; Mintz Levin Cohn Ferris Glovsky and Popeo, P.C.

(57) ABSTRACT

The disclosure provides compositions and methods for making a colorized solution of an aqueous disinfectant that is both stable in bulk solution and will fade to clear within a predetermined period of time after being applied to a surface, for example as a spray or film. The compositions and methods described here allow an end user to visualize both the extent of coverage and the duration of contact of the disinfectant with the surface, thereby providing more efficient disinfection of the surface.

20 Claims, 4 Drawing Sheets

Related U.S. Application Data

(60) Provisional application No. 62/294,465, filed on Feb. 12, 2016.

(51) Int. Cl.
*C11D 9/44* (2006.01)
*C11D 3/04* (2006.01)
*A01N 59/00* (2006.01)
*C11D 3/39* (2006.01)
*C11D 3/395* (2006.01)

(56) References Cited

U.S. PATENT DOCUMENTS

| | | | |
|---|---|---|---|
| 4,308,625 A | | 1/1982 | Kitko |
| 4,353,866 A | | 10/1982 | Wong |
| 4,390,342 A | * | 6/1983 | Bruttel ............... C09B 67/0072 8/524 |
| 4,474,677 A | | 10/1984 | Foxlee |
| 4,605,534 A | | 8/1986 | Meloy |
| 4,623,476 A | | 11/1986 | Nayar et al. |
| 4,822,854 A | | 4/1989 | Ciolino |
| 5,034,150 A | | 7/1991 | Smith |
| 5,064,635 A | | 11/1991 | Casey |
| 5,110,492 A | | 5/1992 | Casey |
| 5,547,662 A | | 8/1996 | Khan |
| 5,556,835 A | * | 9/1996 | Inaoka ...................... A61L 9/01 512/3 |
| 5,670,469 A | | 9/1997 | Dingus |
| 6,362,156 B1 | | 3/2002 | Hsu et al. |
| 6,447,757 B1 | | 9/2002 | Orlowski et al. |
| 6,503,877 B2 | | 1/2003 | Grande et al. |
| 6,677,287 B1 | | 1/2004 | Willman |
| 6,900,167 B2 | | 5/2005 | Griese et al. |
| 7,271,137 B2 | | 9/2007 | Tucker |
| 8,389,463 B2 | | 3/2013 | Mohs et al. |
| 9,101,134 B2 | | 8/2015 | Huang |
| 2001/0051567 A1 | | 12/2001 | Schaschke |
| 2003/0059483 A1 | | 3/2003 | Sowle |
| 2005/0019090 A1 | * | 1/2005 | Takasu .................. B43K 1/086 401/214 |
| 2008/0067470 A1 | * | 3/2008 | Thangaraj .................. A61L 2/18 252/187.21 |
| 2008/0193650 A1 | | 8/2008 | Lyon |
| 2008/0202953 A1 | | 8/2008 | Mueller |
| 2009/0099054 A1 | | 4/2009 | Smith |
| 2010/0032443 A1 | | 2/2010 | Mueller |
| 2010/0069274 A1 | | 3/2010 | Ebine et al. |
| 2013/0058867 A1 | * | 3/2013 | Moro ................... A61K 9/2054 424/9.1 |
| 2014/0057987 A1 | | 2/2014 | Vinson et al. |
| 2014/0100153 A1 | | 4/2014 | Martinez-Crowley |
| 2015/0044144 A1 | | 2/2015 | Lin |
| 2015/0366416 A1 | | 12/2015 | Hoefte |
| 2017/0336372 A1 | * | 11/2017 | Kang ..................... G01N 21/78 |
| 2017/0336373 A1 | * | 11/2017 | Kang ..................... G01N 21/78 |
| 2018/0010080 A1 | * | 1/2018 | Kang ..................... C11D 9/444 |

FOREIGN PATENT DOCUMENTS

| | | |
|---|---|---|
| CN | 102065696 A | 5/2011 |
| CN | 103766402 A | 5/2014 |
| CN | 104054750 A | 9/2014 |
| DE | 10318009 A1 | 11/2004 |
| EP | 1457529 B1 | 9/2004 |
| FR | 2988731 A1 | 10/2013 |
| GB | 2326340 A | 12/1998 |
| RU | 2458706 C1 | 8/2012 |
| WO | WO-2008/147904 A2 | 12/2008 |

* cited by examiner

COMPOSITIONS AND METHODS FOR USE IN SURFACE DECONTAMINATION

CROSS-REFERENCED TO RELATED APPLICATIONS

This application is a continuation of U.S. application Ser. No. 15/541,211, filed on Jun. 30, 2017, which is a national stage entry, filed under 35 U.S.C. § 371, of International Application No. PCT/US2017/017509, filed on Feb. 10, 2017, which claims the benefit of priority from U.S. Provisional Application Ser. No. 62/294,465, filed on Feb. 12, 2016, the entire contents of which are incorporated herein by reference in their entirety.

TECHNICAL FIELD OF THE INVENTION

The invention generally relates to compositions and methods for visualizing disinfectant agents and monitoring disinfectant efficacy.

BACKGROUND OF THE INVENTION

A recent report published in *JAMA Internal Medicine* found that contamination of skin and clothing occurs during glove and gown removal in 60% of cases (M E Tomas, et al. (2015). Contamination of Health Care Personnel During Removal of Personal Protective Equipment. *JAMA Intern Med.* 175(12):1904-10.) When using educational intervention and visual feedback, the study found that the rate of contamination fell to 18.9%. However, providing training on proper personal protective equipment removal is not always feasible, especially in resource-limited settings or during epidemics, and many commonly used disinfectants do not provide visual feedback. Thus, there exists a need for improved methods and techniques to visually ensure proper disinfection to reduce the rate of contamination.

Commercially available products such as Glo Germ™ have demonstrated the importance of visualizing disinfection. For instance, Glo Germ™ has been used in the Mount Sinai Health System to ensure that surfaces are completely disinfected (*The Wall Street Journal*. (2015, Nov. 2)). However, Glo Germ™ requires the use of an ultraviolet light for visualization, which may not be readily available in the field, and requires a power source. In addition, the need to carry around or install an ultraviolet light source can be tedious and infeasible for checking every disinfected surface in a fast-paced hospital setting.

Further studies have also demonstrated that improving compliance with waiting sufficient contact time for a disinfectant to inactivate a pathogen can reduce the rate of hospital-acquired infections by more than 80% (R Orenstein, et al. (2011). *Infect Control Hosp. Epidemiol.* 32(11): 1137-9.) This strongly suggests that a method for improving compliance with contact time is urgently needed to reduce the rate of infection in hospitals, as well as for consumers use.

The inclusion of coloring agents in aqueous bleach solutions has previously been described. Due to the strong tendency of bleach solution to oxidize dyes, many have disclosed methods for the incorporation of coloring agents that are stable in bleach. U.S. Pat. No. 4,623,476 to Nayar teaches a method and composition for the stable suspension of pigments in aqueous hypochlorite bleach solutions, using a bleach-stable pigment (Ultramarine Blue), an optical brightener, and a surfactant. U.S. Pat. No. 6,503,877 to Grande teaches a liquid colored thickened bleach composition that includes Ultramarine Blue as a colorant and a viscosifying surfactant that helps provide stable coloration and viscosity upon prolonged periods of storage. U.S. Pat. No. 4,474,677 to Foxlee describes halogenated copper phthalocyanine pigments for forming blue or green aqueous bleaching solutions. These and similar patents solve the problem of rapid bleaching of dyes by strong oxidants by providing more color-stable compositions which retain their color even after prolonged contact with the oxidant.

Oxidizable dyes have been described in the use of cleaning formulations. U.S. Pat. No. 4,308,625 to Kitko discloses the use of bleach-sensitive dyes in combination with hypochlorite sanitizing agents. Kitko describes a toilet bowl sanitizer in which the oxidizable dye and bleach solution are dispensed upon flushing such that the subsequent fading of the color indicates bleaching action. U.S. Pat. No. 6,447,757 to Orlowski discloses the inclusion of FD&C Blue 1 pigment as a component of a bleach-based teeth-whitening mixture. The decolorization of the dye allows the patient to monitor the occurrence and completion of teeth bleaching activity.

U.S. Pat. No. 4,822,854 to Ciolino describes the use of acidifying agents, such as oxalic acid for preventing impurities within the glycol ether-based disinfectant from reacting with and decolorizing the dye at a pH range of 2 to 6.5. The aim is to prevent unwanted impurities within a disinfectant from reacting with the dye.

U.S. Pat. No. 5,110,492 to Casey discloses the combination of a cleaning composition with a disappearing pH dye that must be sealed in an airtight container. Operating under a similar method, U.S. Pat. Application 2014/0057987 by Vinson discloses the composition of a disinfectant with a pH indicator dye and an alkaline substance. The pH dye initially expresses color upon spraying but rapidly fades to clear upon exposure to the sprayed surface and the air.

There remains a need for new compositions and methods to ensure the thorough and efficient disinfection of surfaces. The present invention addresses this need.

SUMMARY OF THE INVENTION

Figure 1:
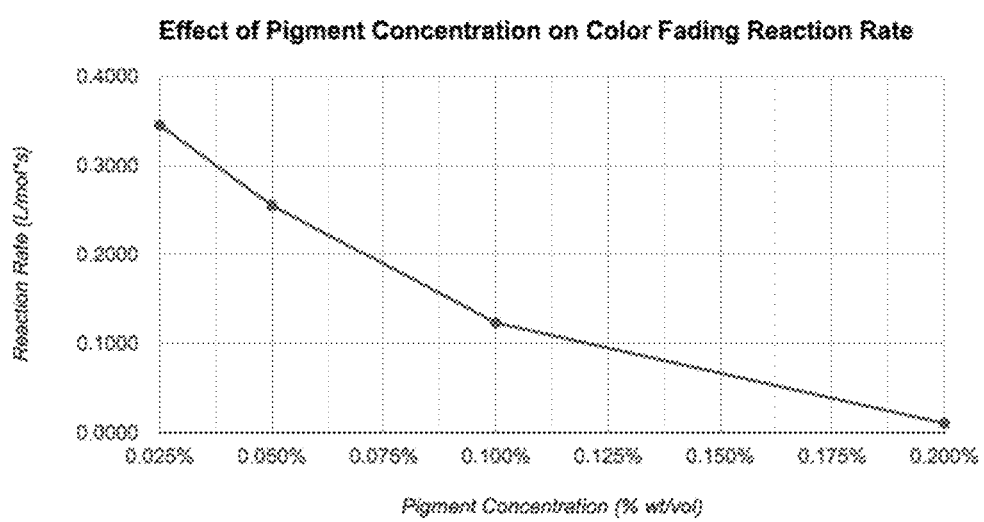
FIG. 1: Line graph representing the effect of changing the concentration of water-soluble pigment FD&C Blue 1 on color fading reaction rate when a composition is added into 0.525% sodium hypochlorite. Reaction rate is obtained based on absorbance measurements over time.

The present disclosure relates to compositions and methods for use in the disinfection and decontamination of surfaces. The compositions described here are adapted to impart a transient color to a typical disinfectant solution such that the disinfectant can be clearly visualized when applied to a surface, in order to ensure complete coverage of the surface. The compositions described here are further adapted to provide for the fading of the color over a predetermined period of time after application to the surface, in order to provide an indication of how long the disinfectant is in contact with the surface. This allows the user to visualize both the extent of coverage and the time of coverage, thereby ensuring adequate decontamination or disinfection of the surface. Typical disinfectant solutions compatible with the compositions described here include aqueous solutions of common disinfecting agents, for example, sodium hypochlorite, calcium hypochlorite, sodium dichloroisocyanurate, hydrogen peroxide, chlorine dioxide, peracetic acid, quaternary ammonium chloride, and alcohols, such as ethanol. The disclosure also provides methods for modulating and controlling the time of color-fading for the oxidizable pigments that are included in the compositions. The compositions and methods described here are suitable for use in both hospital and field settings, as well as for consumer use.

In embodiments, the disclosure provides a solid composition comprising a water-soluble pigment, a surfactant, and optionally one or more of an alkaline builder and a rheology modifier, each present in an amount suitable to color a bulk aqueous solution of sodium or calcium hypochlorite such that the color is stable in the bulk solution for at least from 15 minutes to 6 hours, but which color fades to clear within a predetermined time period of from 1 to 20 minutes, preferably from 2 to 12 minutes, when the solution is applied as a spray or film to a surface. In embodiments, the color is stable in the bulk solution for from about 15 minutes to 6 hours. In embodiments, the bulk aqueous solution is from 1 to 5 gallons. In embodiments, the bulk aqueous solution is 0.1-2% sodium hypochlorite or calcium hypochlorite. In embodiments, the bulk aqueous solution is 0.2-0.5% sodium hypochlorite or calcium hypochlorite.

In embodiments, the ratio of surfactant to water-soluble pigment in the composition is from 0.10:1 to 45:1, preferably from 10:1 to 20:1. In embodiments, the ratio of alkaline builder to water-soluble pigment in the composition is from 0.10:1 to 30:1, preferably from 1:1 to 2:1. In embodiments, the ratio of rheology modifier to water-soluble pigment in the composition is from 0.10:1 to 20:1, preferably from 0.5:1 to 4:1. In embodiments, the total amount of water soluble pigment in the composition is 1-43% w/w, preferably 1-10% w/w, based on total weight of the composition. In embodiments, the total amount of alkaline builder in the composition, if present, is 1-48% w/w, preferably 3-15% w/w, based on total weight of the composition. In embodiments, the total amount of surfactant in the composition is 25-97% w/w, preferably 50-70% w/w, based on total weight of the composition. In embodiments, the total amount of rheology modifier in the composition, if present, is 2-65% w/w, preferably 20-30% w/w, based on total weight of the composition.

In embodiments, the water soluble pigment is selected from FD&C Blue 1, Acid Green 50, Acid Green 25, Patent Blue V, FD&C Yellow 6, Fast Green FCF, Indigo Carmine, Acid Blue 80, Remazol Brilliant Blue R, Coomassie Brilliant Blue, Crystal Violet Lactone, Thymolphthalein, Bromothymol Blue, Methylene Blue, FD&C Red 2, and mixtures thereof.

In embodiments, the surfactant is selected from sodium dodecyl sulfate (SDS) or sodium xylene sulfonate (SXS), sodium laureth sulfate (SLES), sodium myreth sulfate (SMS), sodium cholate, an acetylenic diol (e.g., Surfynol™ 104S), alkyldiphenyloxide disulfonate (e.g., DOWFAX™ 2A1), sodium toluene sulfonate (STS), and mixtures thereof.

In embodiments, the alkaline builder selected from sodium hydroxide (NaOH), calcium hydroxide ($Ca(OH)_2$), potassium hydroxide (KOH), lithium hydroxide (LiOH), and mixtures thereof.

In embodiments, the rheology modifier is selected from sodium alginate, glycerol, guar gum, locust bean, dextran, cellulose, carrageenan (lambda, iota, kappa), sodium carbonate, fumed silica, alkali swellable emulsions, hydrophobically modified alkali swellable emulsions, hydrophobically modified polyurethanes, sodium polyacrylate, and mixtures thereof.

In embodiments, the composition optionally further comprises one or more of a catalyst and a perfume. In embodiments, the catalyst is a reactive oxygen species generating catalyst selected from sodium nitrate, potassium nitrate, sodium nitrite, and titanium dioxide. In embodiments, the total amount of catalyst in the composition, if present, is 3-40% w/w, preferably 3-10% w/w, based on total weight of the composition. In embodiments, the ratio of catalyst to water-soluble pigment in the composition is from 0.50:1 to 5:1. In embodiments, the perfume is selected from citric acid, benzoic acid, and acetic acid. In embodiments, the total amount of perfume in the composition, if present, is 2-30% w/w, preferably 2-10% w/w, based on total weight of the composition. In embodiments, the ratio of perfume to water-soluble pigment in the composition is from 0.25:1 to 20:1, preferably from 0.5:1 to 4:1.

In embodiments, the water soluble pigment is selected from FD&C Blue 1, Acid Green 25, Acid Green 50, Patent Blue V, Fast Green FCF, Acid Blue 80, and mixtures thereof, the surfactant is selected from SDS, SXS, an acetylenic diol, alkyldiphenyloxide disulfonate, and mixtures thereof, the optional alkaline builder is selected from NaOH, $Ca(OH)_2$, and mixtures thereof, and the optional rheology modifier is lambda carrageenan. In embodiments, where the composition comprises an alkaline builder, the total amount of water soluble pigment in the composition is from 2-22% w/w, the total amount of surfactant is from 50-97% w/w, the total amount of alkaline builder is from 1.5-35% w/w, and amount of rheology modifier, if present, is from 10-55% w/w. In embodiments, the predetermined time period is from 2 to 20 minutes. In embodiments, where the composition comprises an alkaline builder and a rheology modifier, the total amount of water soluble pigment in the composition is 2.5-5% w/w, the total amount of surfactant is 50-70% w/w, the total amount of alkaline builder is 3-10%, and the total amount of rheology modifier is 20-35%. In embodiments, the water soluble pigment is Acid Green 50, the surfactant is a mixture of SDS and SXS, the alkaline builder is NaOH, and the rheology modifier is lambda carrageenan. In embodiments, the predetermined time period is from 2 to 5 minutes.

In embodiments, where the composition comprises a rheology modifier, wherein the total amount of water soluble pigment in the composition is from 1.5-22 w/w, the total amount of surfactant is from 10-80% w/w, the total amount of alkaline builder, if present, is from 2-40% w/w, and the amount of rheology modifier is from 1-55% w/w. In embodiments, the composition comprises an alkaline builder. In embodiments, the rheology modifier is selected from lambda carrageenan, sodium alginate, fumed silica, and mixtures thereof. In embodiments, the amount of rheology modifier is 10-65% w/w, preferably 20-65% w/w.

In embodiments, the composition comprises an alkaline builder and further comprises a catalyst, and the total amount of water soluble pigment in the composition is 1-40% w/w, preferably 12-40% w/w, the total amount of surfactant is from 20-90% w/w, the total amount of alkaline builder is 0.5-45% w/w, preferably 15-45% w/w, and amount of catalyst, is 2-40% w/w, preferably 15-40% w/w. In embodiments, the predetermined time period is from 2 to 25 minutes, preferably from 5 to 15 minutes. In embodiments, the catalyst is selected from sodium nitrite, potassium nitrate, titanium dioxide, citric acid, benzoic acid, and acetic acid. In embodiments, the composition comprises 1-D&C Blue 1, SDS, and NaOH.

The disclosure also provides a solid composition comprising at least one water-soluble pigment, at least one surfactant, an alkaline builder, and optionally a rheology modifier, each present in an amount suitable to color a bulk aqueous solution of sodium dichloroisocyanurate (NaDCC) such that the color is stable in the bulk solution for at least 4 to 6 hours, but which color fades to clear within a predetermined time period of from 1 to 15 minutes, when the solution is applied as a spray or film to a surface. In embodiments, the bulk aqueous solution is 0.1-2% NaDCC, preferably 0.5-1% NaDCC. In embodiments, the at least one water-soluble pigment is Acid Green 50. In embodiments, the total amount of water soluble pigment is 1.5-22% w/w, preferably 3-8% w/w, most preferably 4-7% w/w. In embodiments, the at least one surfactant is selected from SDS, SXS, an acetylenic diol, and mixtures thereof. In embodiments, the total amount of surfactant is 10-75% w/w, preferably 40-60% w/w. In embodiments, the alkaline builder is selected from NaOH and Ca(OH)$_2$, and mixtures thereof. In embodiments, the total amount of alkaline builder is from 2.0-50% w/w, preferably 20-50% w/w. In embodiments, the composition comprises a rheology modifier. In embodiments, the rheology modifier is lambda carrageenan and the total amount of rheology modifier is 10-65 w/w, preferably 10-20% w/w. In embodiments, the ratio of surfactant to water-soluble pigment in the composition is from 2:1 to 43:1, preferably from 5:1 to 10:1. In embodiments, the ratio of alkaline builder to water-soluble pigment in the composition is from 0.1:1 to 7:1, preferably from 4:1 to 7:1. In embodiments, the ratio of rheology modifier to water-soluble pigment in the composition is from 0.7:1 to 10:1, preferably from 1:1 to 5:1.

The disclosure also provides a solid composition comprising at least one water-soluble pigment, at least one surfactant, an alkaline builder, and a catalyst, each present in an amount suitable to color a bulk aqueous solution of hydrogen peroxide such that the color is stable in the bulk solution for from at least 20 to 40 minutes, but which color fades to clear within a predetermined time period of from 2 to 20 minutes, when the solution is applied as a spray or film to a surface. In embodiments, the bulk aqueous solution of hydrogen peroxide is 0.5-35%, preferably 3-7.5%, most preferably, 7-8% hydrogen peroxide. In embodiments, the at least one water-soluble pigment is indigo carmine. In embodiments, the total amount of water soluble pigment is from 4-40% w/w, preferably 6-20% w/w. In embodiments, the at least one surfactant is SDS. In embodiments, the total amount of surfactant is from 5-75% w/w, preferably 25-55% w/w. In embodiments, the alkaline builder is NaOH. In embodiments, the total amount of alkaline builder is from 5-30% w/w. In embodiments, the catalyst is selected from copper (II) sulfate pentahydrate and iron (III) nitrate nonahydrate. In embodiments, the total amount of catalyst is from 6-60% w/w, preferably 10-50% w/w. In embodiments, the composition further comprises a rheology modifier. In embodiments, the ratio of surfactant to water-soluble pigment in the composition is from 2.5:1 to 10:1 for formulas added into 7.5% hydrogen peroxide. In embodiments, the ratio of alkaline builder to water-soluble pigment in the composition is from 1:1 to 3:1 for formulas added into 7.5% hydrogen peroxide. In embodiments, the ratio of catalyst to water-soluble pigment in the composition is from 1:1 to 8:1 for formulas added into 7.5% hydrogen peroxide.

The disclosure also provides a solid composition comprising at least one water-soluble pigment, an alkaline builder, and a catalyst, each present in an amount suitable to color a bulk aqueous solution of peracetic acid such that the color is stable in the bulk solution for from at least 10 to 50 minutes, but which color fades to clear within a predetermined time period of from 1 to 10 minutes, when the solution is applied as a spray or film to a surface. In embodiments, the bulk aqueous solution of peracetic acid is 0.1-13%, preferably 0.3-12.5%, most preferably 0.3-0.4% peracetic acid. In embodiments, the at least one water-soluble pigment is FD&C Blue 1. In embodiments, the total amount of water soluble pigment is from 20-50% w/w, preferably 25-40% w/w. In embodiments, the alkaline builder is NaOH. In embodiments, the total amount of alkaline builder is from 20-50% w/w. In embodiments, the catalyst is hexadecyltrimethylammonium bromide (HTAB). In embodiments, the total amount of catalyst is from 20-50% w/w. In embodiments, the ratio of catalyst to water-soluble pigment in the composition is from 0.50:1 to 2:1 for formulas added into 0.3% peracetic acid. In embodiments, the ratio of alkaline builder to water-soluble pigment in the composition is from 0.50:1 to 2:1 for formulas added into 0.3% peracetic acid.

The disclosure also provides an aqueous liquid composition comprising at least one water-soluble pigment and an alkaline builder, each present in an amount suitable to color a bulk aqueous solution of chlorine dioxide such that the color is stable in the bulk solution for at least from 2-3 hours, but which color fades to clear within a predetermined time period of from 5-30 minutes, when the solution is applied as a spray or film to a surface. In embodiments, the bulk aqueous solution of chlorine dioxide is 0.2% chlorine dioxide. In embodiments, the at least one water-soluble pigment is thymolphthalein. In embodiments, the total amount of water soluble pigment is from 1-8% w/w. In embodiments, the alkaline builder is NaOH. In embodiments, the total amount of alkaline builder is from 1-4% w/w. In embodiments, the ratio of water to water-soluble pigment in the composition is from 13:1 to 34:1 for formulas added into 0.2% chlorine dioxide. In embodiments, the ratio of alkaline builder to water-soluble pigment in the composition is from 0.25:1 to 2.6:1, for formulas added into 0.2% chlorine dioxide.

The disclosure also provides an aqueous liquid composition comprising at least one water-soluble pigment, a surfactant, an optional alkaline builder, and an optional rheology modifier, each present in an amount suitable to color a bulk aqueous solution of 0.1-2% sodium hypochlorite or calcium hypochlorite such that the color is stable in the bulk solution for from 10 to 20 minutes, but which color fades to clear within a predetermined time period of from 2 to 5 minutes, when the solution is applied as a spray or film to a surface. In embodiments, the aqueous solution is 0.2-0.5% sodium hypochlorite or calcium hypochlorite. In embodiments, the at least one water-soluble pigment FD&C Blue 1. In embodiments, the total amount of water soluble pigment is from 0.5-2% w/v. In embodiments, the at least one surfactant is selected from SDS, SXS, and mixtures thereof. In embodiments, the total amount of surfactant is from 0.5-1.5% w/v. In embodiments, the alkaline builder is selected from NaOH and LiOH. In embodiments, the total amount of alkaline builder is from 0.5-2% w/v.

In embodiments of the liquid compositions described here, the at least one rheology modifier is selected from sodium alginate and, lambda carrageenan, and mixtures thereof. In embodiments, the total amount of rheology modifier is from 0.1-1% w/v.

In embodiments of the compositions described here, the composition may be packaged in unit form, each unit being suitable as an additive to a bulk aqueous solution of a disinfectant selected from 0.2-0.5% sodium or calcium hypochlorite, 0.5% sodium dichloroisocyanurate, 7-8% hydrogen peroxide, and 0.3% peracetic acid. In embodiments, the unit form is a tablet or capsule. In embodiments, the unit form is a pouch containing a defined quantity of the composition. In embodiments, the pouch is comprised of a water-soluble plastic material. In embodiments, the water-soluble plastic material is PVA. In embodiments, the composition is in the form of a powder, a capsule, or a tablet. In embodiments, the water soluble pigment is pre-processed before incorporating into the composition by being treated with ultraviolet radiation or ozone for a period of about 1 minute to about 72 hours. In embodiments, the water soluble pigment is pre-processed by being dissolved in a solvent at room temperature or at the boiling point, and left as a liquid or evaporated to a powder.

DETAILED DESCRIPTION OF THE INVENTION

The present disclosure provides compositions and methods for visualizing the decontamination or disinfection of a surface. The compositions described here comprise at least one water soluble oxidizable pigment in combination with at least one surfactant or alkaline builder, and mixtures thereof, and optionally, one or more additional ingredients selected from a rheology modifier, a catalyst, and a perfume. The compositions are suitable for addition to a conventional aqueous disinfectant solution of the user's choice, preferably shortly before use, for example within 1 to 60 minutes before use, or immediately before use. The compositions are adapted to impart a color to the bulk solution in its container that is stable for a period of time from minutes to hours, and are further adapted to cause the solution to fade in color to clear within a predetermined period of time from seconds to minutes after application to a surface.

Suitable disinfectant solutions for use with the compositions described here include aqueous solutions of common oxidant-based disinfecting agents, for example, sodium hypochlorite, calcium hypochlorite, sodium dichloroisocyanurate (NaDCC), hydrogen peroxide, chlorine dioxide, peracetic acid, benzalkonium chloride, alkyldimethylbenzylammonium chloride, quaternary ammonium compounds, phenols, and alcohols, such as ethanol and isopropyl alcohol. In embodiments, the disinfectant solution is selected from the group consisting of an aqueous solution of 0.1-2% or 0.2-0.5% sodium or calcium hypochlorite, 0.5% calcium hypochlorite, 0.2% calcium hypochlorite, 0.1-2% NaDCC, 0.5-1% NaDCC, 0.5% NaDCC, 0.1-13%, 0.3-12.5%, or 0.3-0.4% peracetic acid, 0.3% peracetic acid, 0.5-35%, 3-7.5%, or 7-8% hydrogen peroxide, 7.5% hydrogen peroxide, 0.20% chlorine dioxide, 70% ethanol, and 0.4% quaternary ammonium.

The point-of-use additive methodology described here represents a unique approach for controlling the rate of color-fading of an oxidizable pigment in an oxidizing solution. For example, oxidizable dyes degrade rapidly in the presence of a strong oxidizer such as hypochlorous acid, which is a common component of aqueous disinfectant solutions. Oxidizable dyes are therefore generally not suitable for long-term storage in a container of hypochlorous acid. But, as demonstrated here, compositions comprising oxidizable dyes can be adapted to both maintain their color in solution in a bulk container for a period of time ranging from minutes to hours, and also to fade over a predetermined period of time from seconds to minutes to tens of minutes following application of the solution to a surface.

The compositions described here are adapted to provide different durations of color, both in solution in the bulk container, and after application to a surface. For example, a disinfectant solution comprising a composition described here may fade in color within minutes (e.g. 3, 5 or 10 minutes) after its application to a surface, while at the same time persisting in solution in a bulk container for at least a period of 1 to 2 hours, or more. In embodiments using pH sensitive dyes, including without limitation crystal violet lactone, thymolphthalein, and bromothymol blue, the color of the bulk disinfectant solution in a sealed container may be at least 2-6 hours, or at least 6-12 hours, and may be stable for a period of days or weeks, or longer. This is possible in part because the color a disinfectant solution comprising a composition as described herein will fade faster when it is applied to a surface than when it is in solution in a bulk container, due to the higher surface area of the solution that is exposed to air when it is applied to a surface, compared to when it is in the bulk container. Thus, a thin layer of the solution applied to a surface has a greater surface area: volume ratio of exposure to oxygen, carbon dioxide, ultraviolet radiation, light, and heat, compared to the solution in the bulk container, any of which may result in redox reactions, pH changes, and physical changes of state (e.g. evaporation) that serve to fade the color of the oxidizable pigment.

In embodiments, the compositions described here are adapted to provide a duration of color of an oxidizable pigment in an aqueous disinfectant solution for a period of time from about 30 seconds to about 30 minutes after the colored solution is applied to a surface as a thin mist or film. In embodiments, the period of time is selected from 30 seconds to 30 minutes, preferably from about 30 seconds to 3 minutes, 30 seconds to 5 minutes, 5 minutes to 10 minutes, or 10 minutes to 15 minutes. In embodiments, the period of time is about 30 seconds or about 1, 2, 3, 5, 8, 10, 12, 15, or 30 minutes. In embodiments, the period of time is the time required to completely cover a surface and disinfect the surface. The actual time of color duration may be adjusted by addition of dye stabilizers or destabilizers to the composition, as described herein.

Techniques for modulating the time that it takes for the disinfectant color to fade may also be tailored to the user's needs. For example, color fading can be adjusted such that a user decontaminating a large surface can avoid spraying areas that have already been treated based on the presence of color. In another example, a user who is decontaminating donned personal protective equipment (PPE) may require faster color fading such that the PPE can be doffed without the risk of staining the wearer's clothing or skin. In still other cases, an end-user may want to tailor the color-fading to correspond to the contact time needed to inactivate a pathogen, such as a 0.5% sodium hypochlorite solution requiring 3 minutes to kill *Clostridium difficile*.

In embodiments, the water soluble pigment is pre-treated with ultraviolet radiation or ozone for a period between about 1 minute to about 72 hours before addition to a composition as described herein. In another embodiment, the water soluble pigment is pre-treated by dissolution in a suitable solvent (e.g., water, alcohol) at room temperature or at the boiling point, and then evaporating the solution back to a concentrated liquid or powder form. These pre-treatment processes applied to the pigment may be used, for example, to decrease the time needed for the colorized solution to fade to clear following its application to a surface. These techniques have the effect of partially oxidizing or degrading the pigment, making it more susceptible to fading once it is in contact with the oxidant of the disinfectant solution.

The disclosure also provides methods for modulating the color persistence of a water-soluble oxidizable pigment in an aqueous oxidizing solution, for example in a bulk container of a disinfectant described above. In this context, an oxidizing solution contains an oxidizing agent. Exemplary oxidizing agents are those found in conventional disinfectant solutions, as discussed above. In embodiments, the methods comprise sequestering particles of the dye in solution in order to slow their oxidation, for example by including a suitable amount of a surfactant. Without wishing to be bound by theory, surfactant micelles may form an aqueous core that acts to sequester dye particles away from the oxidizing agent of the disinfectant solution, thereby protecting the dye from attack by the oxidizing agent and delaying the eventual degradation of the dye chromophore. In embodiments, the methods comprise lowering the reactivity of the oxidizing agent against the dye particles in solution, for example, by including suitable amounts of an alkaline builder. In embodiments, more than one surfactant or alkaline builder, or both, may be included in the composition.

The presence of an alkaline builder in the composition, either alone or in combination with a surfactant, increases the pH of the solution to slow down the oxidation reaction and thereby slow the decolorization of the pigment. In embodiments, the alkaline builder is present in sufficient amounts to increase the pH of the solution to a range between about pH 9 to about pH 14. For certain disinfectants, such as sodium hypochlorite or calcium hypochlorite, the addition of an alkaline builder as a dye stabilizer functions by shifting the equilibrium of active chemical species towards the less reactive species. For example, sodium hypochlorite (NaOCl) in aqueous solution contains different chlorine species that have different reactivities. HOCl predominates at acidic pH and is roughly 1000 times more reactive than the other species, OCl$^-$, which predominates at basic pH. By incorporating an alkaline builder into a colored disinfectant like sodium or calcium hypochlorite, the ratio of OCl$^-$ to HOCl will increase, resulting in less reactivity towards the dye in solution. Upon application to a surface and exposure to air, without wishing to be bound by theory, acidic $CO_2$ in the air will neutralize the alkalinity, allowing the more reactive HOCl species to dominate and thereby accelerate color fading.

In embodiments, further additives, such as a rheology modifier (also known as a thickening or viscosifying agent), may be included in the composition to slow acidification and thus to slow the reactivity of the oxidizing agent upon exposure to air. The rheology modifier may be in powder or liquid form and upon addition, function to increase the viscosity of the disinfectant solution. Due to increased viscosity, contact of the solution with air and $CO_2$ is impeded, thus slowing down acidification of the solution. In certain disinfectants, slowing down the rate of acidification upon exposure to air allows water-soluble dye in the solution to fade at a slower rate. For example, a more viscous calcium hypochlorite disinfectant containing a dye indicator will fade in color more slowly due to slower generation of HOCl. A higher viscosity also may also impede physical interactions between an oxidizable dye and an oxidizer, thereby also slowing down the rate of color-fading.

In embodiments, a source of reactive oxygen species (ROS), such as a catalyst that generates ROS, may be included in the composition to accelerate color fading. Certain cationic surfactants can catalyze the generation of ROS. One example is hexadecyltrimethylammonium bromide (HTAB), which generates hydroxyl radicals in disinfectants like peracetic acid or hydrogen peroxide.

Other adjuvants, such as perfumes in powdered or liquid form, may also be included in the compositions described here. A perfume may act to stabilize or destabilize a water-soluble pigment. The addition of a perfume to disinfectants may neutralize otherwise harmful odors in disinfectants such as sodium and calcium hypochlorite, which have been reported to irritate the skin, eyes, and lungs of healthcare workers in the field and patients in hospitals. Without wishing to be bound by theory, certain water-soluble perfumes may dissociate into ions in solution to electrochemically repel similarly charged particles, such as anionic surfactants and OCl$^-$, hindering the interaction between oxidizing agents and water soluble dyes. On an atomic level, the addition of perfumes may also act as an impurity to sterically impede the reaction between oxidizing agents and the dye chromophore. Still another embodiment is the ability of some perfumes to modify the pH of the solution, such as about 0.01% to about 10% citric acid, which acts both to add a citrus scent to the disinfectant and lower the pH to speed up the color-fading reaction of disinfectants like sodium and calcium hypochlorite.

Generally, the water-soluble pigment for use in the compositions and methods described here may be selected from FD&C Blue 1, Fast Green FCF, erythrosine, 40 FD&C Red 40, FD&C Red 2, FD&C Yellow 5, FD&C Yellow 6, Indigo carmine, ultramarine, cobalt blue, phthalocyanine, and Coomassie Brilliant Blue, Acid Green 25, Bromothymol Blue, Acid Green 50, Acid Blue 80, Remazol Brilliant Blue R, Crystal Violet Lactone, Patent Blue V, and thymolphthalein.

Generally, the surfactant for use in the compositions and methods described here may be selected from sodium dodecyl sulfate (SDS), sodium dodecylbenzenesulfonate, sodium 3,4-dichlorobenzoate, sodium laureth sulfate (SLES), acetylenic diols, sodium xylene sulfonate (SXS), and sodium toluene sulfonate (STS). In embodiments where the composition is a solid form, such as a tablet or powder, the surfactant is also a solid form, such as SDS or SXS. In embodiments where the composition is a concentrated liquid, a liquid-based surfactant may be used, such as sodium laureth sulfate (SLES) or DOWFAX 2A1.

Generally, the alkaline builder for use in the compositions and methods described here may be selected from sodium hydroxide, lithium hydroxide, calcium hydroxide, and potassium hydroxide. In embodiments, the alkaline builder is sodium hydroxide or calcium hydroxide.

Generally, the rheology modifier for use in the compositions and methods described here may be selected from sodium alginate, glycerol, guar gum, locust bean, dextran, cellulose, carrageenan (lambda, iota, kappa), fumed silica, alkali swellable emulsions, hydrophobically modified alkali swellable emulsions, hydrophobically modified polyurethanes, and sodium polyacrylate. In embodiments, the rheology modifier is sodium alginate or lambda carrageenan.

Generally, the catalyst for use in the compositions and methods described here is a ROS generating catalyst selected from sodium nitrate, potassium nitrate, sodium nitrite, hexadecyltrimethylammonium bromide (HTAB), copper (II) sulfate pentahydrate, and iron (III) nitrate nonahydrate.

Generally, the perfume for use in the compositions and methods described here may be selected from citric acid, anise oil, pinene, bay leaf oil, benzoic acid, acetic acid, camphor oil, florex, geraniol oil, grapefruit oil, juniper lactone, lemon oil, myristic acid, orange oil terpenes, sandalwood, and vanillin.

In general, a composition described here comprises a water soluble pigment and a surfactant or an alkaline builder, or both, and optionally further comprising one or more additional excipients selected from a rheology modifier, a catalyst, and a perfume. In embodiments, the compositions may contain two or more different pigments, surfactants, or alkaline builders.

The compositions described here may be in solid or liquid form. Solid forms may be, for example, in the form of a powder or tablet which readily dissolves in aqueous solution, typically within seconds, or within less than 60 seconds or less than 30 seconds. Liquid forms are preferably in the form of a concentration solution. The compositions may also be provided in a water-soluble packaging, such as polyvinyl alcohol (PVA) plastic wrapping. In certain embodiments, a composition described here may be impregnated onto a solid form, such as a fabric or mesh, and provided for example as a pre-packaged wipe which is dipped into an aqueous disinfectant solution and then applied to a surface. In certain embodiments, the additive can be part of a dispenser for wipes or hand sanitizers to be added at point of use; or directly mixed into the wipes or hand sanitizers.

In general, the workable ranges of the oxidizable pigment, surfactant, alkaline builder, and other optional excipients will vary depending on both the strength of the oxidizing solution and the desired period of time for color persistence in the bulk solution of disinfectant in its container as well as the desired period of time to fade after the solution is applied to a surface, both of which can be "tuned" or adapted. Illustrative embodiments of how the compositions described here can be adapted for different disinfecting agents to provide different times of color persistence in the bulk solution and different times to fade after application to a surface are described in the embodiments below, and in the Examples. In general, for the same disinfecting agent of a different strength, the same compositions as described below may be used, but more or less of the composition will be added to the disinfecting solution, depending on whether it is more or less dilute than the illustrative embodiments provided here. For example, a solid composition as described here may generally be added to an aqueous solution of 0.5% sodium or calcium hypochlorite in an amount of from 0.5 to 5% w/v. This amount can be adjusted up or down for more concentrated or more dilute solutions of the disinfectant. Since the compositions described here are adapted to impart a bright color to the disinfectant solution, it is possible for the user to visualize how much of the composition to add to disinfectants of differing strengths, for example by comparison to a color panel provided on a product package. Similarly, for a 0.5% NaDCC solution, a composition described here may be added in an amount of from 1 to 5% w/v; for a 0.3% peracetic acid solution, the amount is in the range of 0.3 to 1% w/v; for a 0.20% chlorine dioxide solution, the amount is in the range of 3 to 15% w/v; and for a 7.5% hydrogen peroxide solution, the amount is in the range of from 1 to 4.5% w/v.

Hypochlorite Formulations

In embodiments, the disclosure provides a solid composition for use in an aqueous solution of sodium or calcium hypochlorite, preferably a solution of from 0.1 to 2% or from 0.2 to 0.5% sodium or calcium hypochlorite, or a solution of 0.5% sodium or calcium hypochlorite. These compositions are adapted to provide color stability in the bulk solution for from 15 minutes to 6 hours, and fade to clear times of from 1 to 20 minutes, or from 2 to 12 minutes, after the solution is applied as a spray or film to a surface. In embodiments using pH sensitive dyes, including without limitation Crystal Violet Lactone, Thymolphthalein, and Bromothymol Blue, the color stability in the bulk disinfectant solution is at least 2-6 hours, or at least 6-12 hours, and may be for a period of days or weeks, or longer provided the container sealed and substantially impermeable to air.

In embodiments, the solid composition comprises a water-soluble pigment, a surfactant, and optionally one or more of an alkaline builder and a rheology modifier. Generally, the ratio of surfactant to water-soluble pigment in the composition is from 0.1:1 to 45:1, preferably from 10:1 to 20:1; the ratio of alkaline builder to water-soluble pigment is from 0.1:1 to 30:1, preferably from 1:1 to 2:1; and the ratio of rheology modifier to water-soluble pigment is from 0.1:1 to 20:1, preferably from 0.5:1 to 4:1. The total amount of water soluble pigment in the composition may be from 1-43% w/w, preferably 1-10% w/w, based on total weight of the composition. The total amount of alkaline builder in the composition, if present, may be from 1-48% w/w, preferably 3-15% w/w. The total amount of surfactant in the composition may be from 25-97% w/w, preferably 50-70% w/w. The total amount of rheology modifier in the composition, if present, may be from 2-65% w/w, preferably 20-30% w/w.

In embodiments, the water soluble pigment for use in a solution of sodium or calcium hypochlorite is selected from the water soluble pigment is selected from FD&C Blue 1, Acid Green 25, Acid Green 50, Patent Blue V, FD&C Yellow 5, FD&C Yellow 6, Fast Green FCF, Indigo Carmine, Acid Blue 80, Remazol Brilliant Blue R, Coomassie Brilliant Blue, Crystal Violet Lactone, Thymolphthalein, Bromothymol Blue, Methylene Blue, FD&C Red 2, and mixtures thereof.

In embodiments, the surfactant is selected from sodium dodecyl sulfate (SDS) or sodium xylene sulfonate (SXS), sodium laureth sulfate (SLES), sodium myreth sulfate (SMS), sodium cholate, an acetylenic diol (e.g., Surfynol™ 104S), alkyldiphenyloxide disulfonate (e.g., DOWFAX™ 2A1), sodium toluene sulfonate (STS), and mixtures thereof.

In embodiments, the alkaline builder may be selected from sodium hydroxide (NaOH), calcium hydroxide (Ca (OH)$_2$), potassium hydroxide (KOH), lithium hydroxide (LiOH), and mixtures thereof.

In embodiments, the rheology modifier may be selected from sodium alginate, glycerol, guar gum, dextran, cellulose, carrageenan (lambda, iota, kappa), sodium carbonate, fumed silica, alkali swellable emulsions, hydrophobically modified alkali swellable emulsions, hydrophobically modified polyurethanes, sodium polyacrylate, and mixtures thereof.

In embodiments, the solid composition further comprises one or more of a catalyst and a perfume. In embodiments, the catalyst is a reactive oxygen species generating catalyst selected from sodium nitrate, potassium nitrate, sodium nitrite, and titanium dioxide. In embodiments, the total amount of catalyst in the composition, if present, is 3-40% w/w, preferably 3-10% w/w, based on total weight of the composition. In embodiments, the ratio of catalyst to water-soluble pigment in the composition is from 0.5:1 to 5:1. In embodiments, the perfume may be selected from citric acid, benzoic acid, and acetic acid. In embodiments, the total amount of perfume in the composition, if present, is 2-30% w/w, preferably 2-10% w/w, based on total weight of the composition. In embodiments, the ratio of perfume to water-soluble pigment in the composition is from 0.25:1 to 20:1, preferably from 0.5:1 to 4:1.

In an embodiment, the composition comprises (all percentages are w/w) 4.39% Acid Green 50, 21.93% SDS, 43.86% SXS, 7.89% NaOH, and 21.93% lambda carrageenan. This composition provides a colorized solution of 0.525% sodium hypochlorite or calcium hypochlorite that is color stable for about 360 minutes. When applied to a surface, the color fades within about 3 minutes.

In an embodiment, the composition comprises (all percentages are w/w) 3.02% Acid Green, 1.81% SDS, 60.42% SXS, 4.53% NaOH, and 30.21% w/w lambda carrageenan. This composition provides a colorized solution of 0.525% sodium hypochlorite or calcium hypochlorite that is color stable for about 360 minutes. When applied to a surface the color fades within about 3 minutes.

In an embodiment, the composition comprises (all percentages are w/w) 4.08% Patent Blue V, 81.63% SDS, and 14.29% NaOH. This composition provides a colorized solution of 0.525% sodium hypochlorite or calcium hypochlorite that is color stable for about 130 minutes. When applied to a surface, the color fades within about 18 minutes.

In an embodiment, the composition comprises (all percentages are w/w) 4.55% w/w FD&C Blue 1, 90.91% w/w SDS, and 4.55% w/w Ca(OH)$_2$. This composition provides a colorized solution of 0.525% sodium hypochlorite or calcium hypochlorite that is color stable for about 180 minutes. When applied to a surface, the color fades within about 6 minutes.

In an embodiment, the composition comprises (all percentages are w/w) 5.88% FD&C Blue 1, 88.24% SXS, and 5.88% NaOH. This composition provides a colorized solution of 0.525% sodium hypochlorite or calcium hypochlorite that is color stable for about 35 minutes. When applied to a surface, the color fades within about 6 minutes.

In an embodiment, the composition comprises (all percentages are w/w) 5.13% FD&C Blue 1, 89.74% STS, and 5.13% NaOH. This composition provides a colorized solution of 0.525% sodium hypochlorite or calcium hypochlorite that is color stable for about 13 minutes. When applied to a surface, the color fades within about 5 minutes.

In an embodiment, the composition comprises (all percentages are w/w) 4.88% FD&C Blue 1, 90.24% SLES, and 4.88% NaOH. This composition provides a colorized solution of 0.525% sodium hypochlorite or calcium hypochlorite that is color stable for about 20 minutes. When applied to a surface, the color fades within about 4 minutes.

In an embodiment, the composition comprises (all percentages are w/w) 28.26% FD&C Yellow 5, 67.39% SDS, and 4.35% NaOH. This composition provides a colorized solution of 0.525% sodium hypochlorite or calcium hypochlorite that is color stable for about 25 minutes. When applied to a surface, the color fades within about 80 seconds.

In an embodiment, the composition comprises (all percentages are w/w) 8.70% Fast Green FCF, 86.96% SDS, and 4.35% NaOH. This composition provides a colorized solution of 0.525% sodium hypochlorite or calcium hypochlorite that is color stable for about 45 minutes. When applied to a surface, the color fades within about 5 minutes.

In an embodiment, the composition comprises (all percentages are w/w) 42.62% Indigo Carmine, 49.18% SDS, and 8.20% NaOH. This composition provides a colorized solution of 0.525% sodium hypochlorite or calcium hypochlorite that is color stable for about 2 minutes. When applied to a surface, the color fades within about 25 minutes.

In an embodiment, the composition comprises (all percentages are w/w) 4.44% Acid Blue 80, 80.00% SDS, and 15.56% NaOH. This composition provides a colorized solution of 0.525% sodium hypochlorite or calcium hypochlorite that is color stable for about 180 minutes. When applied to a surface, the color fades within about 7 minutes.

In an embodiment, the composition comprises (all percentages are w/w) 13.33% Remazol Brilliant Blue R, 77.78% SDS, and 8.89% NaOH. This composition provides a colorized solution of 0.525% sodium hypochlorite or calcium hypochlorite that is color stable for about 290 minutes. When applied to a surface, the color fades within about 9 minutes.

In an embodiment, the composition comprises (all percentages are w/w) 5.94% Acid Green 25, 89.11% SDS, and 4.95% NaOH. This composition provides a colorized solution of 0.525% sodium hypochlorite or calcium hypochlorite that is color stable for about 300 minutes. When applied to a surface, the color fades within about 11 minutes.

In an embodiment, the composition comprises (all percentages are w/w) 6.15% Crystal Violet Lactone, 90.00% SDS, and 3.85% NaOH. This composition provides a colorized solution of 0.525% sodium hypochlorite or calcium hypochlorite that is color stable for about 6 hours. When applied to a surface, the color fades within about 1 minute.

In an embodiment, the composition comprises (all percentages are w/w) 4.76% Thymolphthalein, 47.62% SDS, and 47.62% NaOH. This composition provides a colorized solution of 0.525% sodium hypochlorite or calcium hypochlorite that is color stable for about 6 hours. When applied to a surface, the color fades within about 3 minutes.

In an embodiment, the composition comprises (all percentages are w/w) 11.30% Bromothymol Blue, 69.35% SDS, and 19.35% NaOH. This composition provides a colorized solution of 0.525% sodium hypochlorite or calcium hypochlorite that is color stable for about 6 hours. When applied to a surface, the color fades within about 30 seconds.

In an embodiment, the composition comprises (all percentages are w/w) 4.35% FD&C Blue 1, 89.96% SDS, and 5.70% KOH. This composition provides a colorized solution of 0.525% sodium hypochlorite or calcium hypochlorite that is color stable for about 45 minutes. When applied to a surface, the color fades within about 10 minutes.

In an embodiment, the composition comprises (all percentages are w/w) 5.00% FD&C Blue 1, 75.00% SDS, 5.00% NaOH, and 15.00% Sodium alginate. This composition provides a colorized solution of 0.525% sodium hypochlorite or calcium hypochlorite that is color stable for about 30 minutes. When applied to a surface, the color fades within about 5 minutes.

In an embodiment, the composition comprises (all percentages are w/w) 5.36% FD&C Blue 1, 78.90% SDS, 5.26% NaOH, and 10.50% Lambda Carrageenan. This composition provides a colorized solution of 0.525% sodium hypochlorite or calcium hypochlorite that is color stable for about 45 minutes. When applied to a surface, the color fades within about 25 minutes.

In an embodiment, the composition comprises (all percentage are w/w) 14.93% FD&1 Blue 1, 67.16% SDS, 14.93% NaOH, and 2.99% fumed silica. This composition provides a colorized solution of 0.525% sodium hypochlorite or calcium hypochlorite that is color stable for about 30 minutes. When applied to a surface, the color fades within about 11 minutes.

In an embodiment, the composition comprises (all percentages are w/w) 2.70% FD&C Blue 1, 40.50% SDS, 6.80% NaOH, 2.70% Sodium alginate, 6.80% Lambda carrageenan, and 40.50 w/w Fumed Silica. This composition provides a colorized solution of 0.525% sodium hypochlorite or calcium hypochlorite that is color stable for about 30 minutes. When applied to a surface, the color fades within about 12 minutes.

In an embodiment, the composition comprises (all percentages are w/w) 2.82% FD&C Blue 1, 66.10% SDS, 16.95% NaOH, and 14.12% Sodium Polyacrylate. This composition provides a colorized solution of 0.525% sodium hypochlorite or calcium hypochlorite that is color stable for about 3 hours. When applied to a surface, the color fades within about 17 minutes.

In an embodiment, the composition comprises (all percentages are w/w) 5.80% FD&C Blue 1, 43.48% SDS, 21.74% NaOH, and 28.99% Potassium Nitrate. This composition provides a colorized solution of 0.525% sodium hypochlorite or calcium hypochlorite that is color stable for about 40 minutes. When applied to a surface, the color fades within about 10 minutes.

In an embodiment, the composition comprises (all percentages are w/w) 7.41% FD&C Blue 1, 74.07% SDS, 11.11% NaOH, and 7.41% Sodium Nitrite. This composition provides a colorized solution of 0.525% sodium hypochlorite or calcium hypochlorite that is color stable for about 50 minutes. When applied to a surface, the color fades within about 15 minutes.

In an embodiment, the composition comprises (all percentages are w/w) 7.95% FD&C Blue 1, 74.10% SDS, 5.13% NaOH, and 12.82% Citric Acid. This composition provides a colorized solution of 0.525% sodium hypochlorite or calcium hypochlorite that is color stable for about 30 minutes. When applied to a surface, the color fades within about 6 minutes.

In an embodiment, the composition comprises (all percentages are w/w) 4.11% FD&C Blue 1, 13.70% SDS, 41.10% SXS, 13.70% Sodium alginate, and 41.10% Sodium carbonate. This composition provides a colorized solution of 0.525% sodium hypochlorite or calcium hypochlorite that is color stable for about 27 minutes. When applied to a surface, the color fades within about 15 minutes.

In an embodiment, the composition comprises (all percentages are w/w) 4.76% FD&C Blue 1, 57.82% SDS, 34.01% NaOH, and 3.41% Titanium Dioxide. This composition provides a colorized solution of 0.525% sodium hypochlorite or calcium hypochlorite that is color stable for about 30 minutes. When applied to a surface, the color fades within about 4 minutes.

In an embodiment, the composition comprises (all percentages are w/w) 27.27% Methylene Blue, 63.64% SDS, and 9.09% NaOH. This composition provides a colorized solution of 0.525% sodium hypochlorite or calcium hypochlorite that is color stable for about 160 minutes. When applied to a surface, the color fades within about 13 minutes.

In an embodiment, the composition comprises (all percentages are w/w) 19.08% FD&C Red 2, 76.34% SDS, and 4.58% NaOH. This composition provides a colorized solution of 0.525% sodium hypochlorite or calcium hypochlorite that is color stable for about 2 minutes. When applied to a surface, the color fades within about 1 minute.

In an embodiment, the composition comprises 1.50% FD&C Blue 1, 0.75% SXS, 0.35% lambda carrageenan, and 97.40% water. This composition provides a colorized solution of 0.525% sodium hypochlorite or calcium hypochlorite that is color stable for about 240 min. When applied to a surface, the color fades within 4 minutes.

In embodiments, the disclosure provides a liquid composition for use in an aqueous solution of sodium or calcium hypochlorite, preferably a solution of from 0.1 to 2% or from 0.2 to 0.5% sodium or calcium hypochlorite, or a solution of 0.5% sodium or calcium hypochlorite. These compositions are adapted to provide color stability in the bulk solution for from 10 to 20 minutes, and fade to clear times of from 2 to 5 minutes, after the solution is applied as a spray or film to a surface. In embodiments, the at least one water-soluble pigment is FD&C Blue 1. In embodiments, the total amount of water soluble pigment is from 0.5-2% w/v. In embodiments, the at least one surfactant is selected from SDS, SXS, and mixtures thereof. The total amount of surfactant is from 0.5-1.5% w/v. In embodiments, the alkaline builder is selected from NaOH and LiOH. In embodiments, the total amount of alkaline builder is from 0.5-2% w/v.

In embodiments, the disclosure provides a liquid composition for use in a pre-moistened wipe impregnated with sodium hypochlorite solution, preferably a solution from 0.1 to 2% or from 0.2% to 0.65% sodium hypochlorite, or 0.55% or 0.65% sodium hypochlorite. These compositions are adapted to provide color stability on the wipe for from 5 to 10 minutes, and fade to clear times of from 1 to 5 minutes after being applied as a film to a surface. In embodiments, the at least one water-soluble pigment is FD&C Blue 1. In embodiments, the total amount of water soluble pigment is from 0.5-2.5% w/v. In embodiments, the at least one surfactant is selected from SDS, SXS, and mixtures thereof. The total amount of surfactant is from 0.25-1.5% w/v. In embodiments, the alkaline builder is selected from NaOH and LiOH. In embodiments, the total amount of alkaline builder is from 0-2% w/v. In embodiments, the rheology modifier is selected from sodium alginate and lambda carrageenan. In embodiments, the total amount of rheology modifier is from 0-1% w/v.

Sodium Dichloroisocyanurate (NaDCC) Formulations

In embodiments, the disclosure provides a solid composition for use in a bulk aqueous solution of sodium dichloroisocyanurate (NaDCC). Generally, the composition comprises at least one water-soluble pigment, at least one surfactant, an alkaline builder, and optionally a rheology modifier, each present in an amount suitable to provide color stability in the bulk solution for 4 to 6 hours, and to provide a color that fades to clear within a predetermined time period of from 1 to 15 minutes, when the solution is applied as a spray or film to a surface. The bulk aqueous solution may be 0.1 to 2% NaDCC, or 0.5 to 1% NaDCC. In embodiments, the water soluble pigment is Acid Green 50. In embodiments, the total amount of water soluble pigment is 1.5-22% w/w, preferably 3-8% w/w, most preferably 4-7% w/w. In embodiments, the at least one surfactant is selected from SDS, SXS, an acetylenic diol, and mixtures thereof. In embodiments, the total amount of surfactant is 10-75% w/w, preferably 40-60% w/w. In embodiments, the alkaline builder is selected from NaOH and Ca(OH)$_2$, and mixtures thereof. In embodiments, the total amount of alkaline builder is from 2.0-50% w/w, preferably 20-50% w/w. In embodiments, the composition comprises a rheology modifier. In embodiments, the rheology modifier is lambda carrageenan and the total amount of rheology modifier is 10-65 w/w, preferably 10-20% w/w. In embodiments, the ratio of surfactant to water-soluble pigment in the composition is from 2:1 to 43:1, preferably from 5:1 to 10:1. In embodiments, the ratio of alkaline builder to water-soluble pigment in the composition is from 0.1:1 to 7:1, preferably from 4:1 to 7:1. In embodiments, the ratio of rheology modifier to water-soluble pigment in the composition is from 0.7:1 to 10:1, preferably from 1:1 to 5:1.

In an embodiment, the composition comprises (all percentages are w/w) 4.00% Acid Green 50, 16.00% SDS, 6.00% Surfynol™ 104S, 32.00% SXS, 24.00% NaOH, 4.00% Ca(OH)$_2$, 14.00% Lambda Carrageenan. This composition provides a colorized solution of 0.5% NaDCC that is color stable for about 6 hours. When applied to a surface, the color fades within about 5 minutes.

In an embodiment, the composition comprises (all percentages are w/w) Acid 6.67% Green 50, 13.33% SDS, 33.33% NaOH, and 46.67% Guar Gum. This composition provides a colorized solution of 0.5% NaDCC that is color stable for about 4 hours. When applied to a surface, the color fades within about 7 minutes.

In an embodiment, the composition comprises (all percentages are w/w) Acid 6.67% Green 50, 13.33% SDS, 26.67% NaOH, and 33.33% Locust Bean. This composition provides a colorized solution of 0.5% NaDCC that is color stable for about 4 hours. When applied to a surface, the color fades within about 10 minutes.

Peracetic Acid Formulations

In embodiments, the disclosure provides a solid composition for use in a bulk aqueous solution of peracetic acid. Generally, the composition comprises at least one water-soluble pigment, an alkaline builder, and a catalyst, each present in an amount suitable to color a bulk aqueous solution of peracetic acid such that the color is stable in the bulk solution for from 10 to 50 minutes, but which color fades to clear within a predetermined time period of from 1 to 10 minutes, when the solution is applied as a spray or film to a surface. In embodiments, the bulk aqueous solution of peracetic acid is 0.1-13%, preferably 0.3-12.5%, most preferably 0.3-0.4% peracetic acid. In embodiments, the at least one water-soluble pigment is FD&C Blue 1. In embodiments, the total amount of water soluble pigment is from 20-50% w/w, preferably 25-40% w/w. In embodiments, the alkaline builder is NaOH. In embodiments, the total amount of alkaline builder is from 20-50% w/w. In embodiments, the catalyst is hexadecyltrimethylammonium bromide (HTAB). In embodiments, the total amount of catalyst is from 20-50% w/w. In embodiments, the ratio of catalyst to water-soluble pigment in the composition is from 0.50:1 to 2:1 for formulas added into 0.3% peracetic acid. In embodiments, the ratio of alkaline builder to water-soluble pigment in the composition is from 0.50:1 to 2:1 for formulas added into 0.3% peracetic acid.

In an embodiment, the composition comprises (all percentages are w/w) 40% FD&C Blue 1, 20% HTAB, and 40% NaOH. This composition provides a colorized solution of 0.3% peracetic acid that is color stable for about 50 minutes. When applied to a surface, the color fades within about 10 minutes.

In an embodiment, the composition comprises (all percentages are w/w) 33.33% FD&C Blue 1, 33.33% HTAB, and 33.33% NaOH. This composition provides a colorized solution of 0.3% peracetic acid that is color stable for about 30 minutes. When applied to a surface, the color fades within about 5 minutes.

In an embodiment, the composition comprises (all percentages are w/w) 25% FD&C Blue 1, 50% HTAB, and 25% NaOH. This composition provides a colorized solution of 0.3% peracetic acid that is color stable for about 10 minutes. When applied to a surface, the color fades within about 2 minutes.

Chlorine Dioxide Liquid Formulations

In embodiments, the disclosure provides an aqueous liquid composition for use in a bulk aqueous solution of chlorine dioxide. Generally, the composition comprises at least one water-soluble pigment and an alkaline builder, each present in an amount suitable to color a bulk aqueous solution of chlorine dioxide such that the color is stable in the bulk solution for from 2-3 hours, but which color fades to clear within a predetermined time period of from 5-30 minutes, when the solution is applied as a spray or film to a surface. In embodiments, the bulk aqueous solution of chlorine dioxide is 0.2% chlorine dioxide. In embodiments, the at least one water-soluble pigment is thymolpthalein. In embodiments, the total amount of water soluble pigment is from 1-8% w/w. the alkaline builder is NaOH. In embodiments, the total amount of alkaline builder is from 1-4% w/w. In embodiments, the ratio of water to water-soluble pigment in the composition is from 13:1 to 34:1 for formulas added into 0.2% chlorine dioxide. In embodiments, the ratio of alkaline builder to water-soluble pigment in the composition is from 0.25:1 to 2.6:1, for formulas added into 0.2% chlorine dioxide.

In an embodiment, the composition comprises (all percentages are w/w) 3.74% Thymolpthalein, 93.46% water, and 2.8% NaOH. This composition provides a colorized solution of 0.2% chlorine dioxide that is color stable for about 120 minutes. When applied to a surface, the color fades within about 15 minutes.

Hydrogen Peroxide Formulations

In embodiments, the disclosure provides a solid composition for use in a bulk aqueous solution of hydrogen peroxide. Generally, the composition comprises at least one water-soluble pigment, at least one surfactant, an alkaline builder, and a catalyst, each present in an amount suitable to color a bulk aqueous solution of hydrogen peroxide such that the color is stable in the bulk solution for from 20 to 40 minutes, but which color fades to clear within a predetermined time period of from 2 to 20 minutes, when the solution is applied as a spray or film to a surface. In embodiments, the bulk aqueous solution of hydrogen peroxide is 0.5-35%, 3-7.5%, or 7-8% hydrogen peroxide. In embodiments, the at least one water-soluble pigment is indigo carmine. In embodiments, the total amount of water soluble pigment is from 4-40% w/w, preferably 6-20% w/w. In embodiments, the at least one surfactant is SDS. In embodiments, the total amount of surfactant is from 5-75% w/w, preferably 25-55% w/w. In embodiments, the alkaline builder is NaOH. In embodiments, the total amount of alkaline builder is from 5-30% w/w. In embodiments, the catalyst is selected from copper (II) sulfate pentahydrate and iron (III) nitrate nonahydrate. In embodiments, the total amount of catalyst is from 6-60% w/w, preferably 10-50% w/w. In embodiments, the composition further comprises a rheology modifier. In embodiments, the ratio of surfactant to water-soluble pigment in the composition is from 2.5:1 to 10:1 for formulas added into 7.5% hydrogen peroxide. In embodiments, the ratio of alkaline builder to water-soluble pigment in the composition is from 1:1 to 3:1 for formulas added into 7.5% hydrogen peroxide. In embodiments, the ratio of catalyst to water-soluble pigment in the composition is from 1:1 to 8:1 for formulas added into 7.5% hydrogen peroxide.

In an embodiment, the composition comprises (all percentages are w/w) 11.43% Indigo Carmine, 57.14% SDS, 17.14% NaOH, and 14.29% Copper (II) sulfate pentahydrate. This composition provides a colorized solution of 7.5% hydrogen peroxide that is color stable for about 25 minutes. When applied to a surface, the color fades within about 5 minutes.

In an embodiment, the composition comprises (all percentages are w/w) 6.9% Indigo Carmine, 34.48% SDS, 6.9% NaOH, and 51.72% Iron (III) nitrate nonahydrate. This composition provides a colorized solution of 7.5% hydrogen peroxide that is color stable for about 20 minutes. When applied to a surface, the color fades within about 3 minutes.

Alcohol Formulations

In embodiments, the composition is a solid material, such as a dry powder or tablet, suitable for use as an indicator in an aqueous disinfectant solution of an alcohol, such as ethanol. In embodiments, the solution is an aqueous disinfectant solution of 70% ethanol. In embodiments, the composition comprises a water soluble pigment and an alkaline builder, the water soluble pigment being present in an amount of from 30-50 w/w and the alkaline builder being present in an amount of from 30-50 w/w, based on the total weight of the composition. In embodiments, the water soluble pigment is thymolpthalein and the alkaline builder is sodium hydroxide (NaOH), each present in an amount of from 30-50% w/w.

Quaternary Ammonium Formulations

In embodiments, the composition is a solid material, such as a dry powder or tablet, suitable for use as an indicator in an aqueous disinfectant solution of a quaternary ammonium compound. In embodiments, the solution is an aqueous disinfectant solution of 0.4% quaternary ammonium. In embodiments, the composition comprises a water soluble pigment and an alkaline builder, the water soluble pigment being present in an amount of from 30-50% w/w and the alkaline builder being present in an amount of from 30-50 w/w, based on the total weight of the composition. In embodiments, the water soluble pigment is thymolpthalein and the alkaline builder is sodium hydroxide (NaOH), each present in an amount of from 30-50% w/w.

TABLE 1

Some general formulas based on the examples. Abbreviations are sodium dodecyl sulfate (SDS), sodium xylene sulfonate (SXS), sodium hydroxide (NaOH), calcium hydroxide (Ca(OH)$_2$).

| | | | % Wt./Wt | | | | |
|---|---|---|---|---|---|---|---|
| Disinfectant solution | Pigment | Surfactant | Alkaline Builder | Rheology Modifier | Catalyst | Perfume | Examples |
| 0.525% sodium hypochlorite | FD&C Blue 1 (4.0-5.0) | SDS (80.0-85.0) | NaOH (7.0-8.0) | Sodium alginate (20.0-25.0) | — | — | 20 |
| 0.525% sodium hypochlorite | Acid Green 50 (3.0-5.0) | SDS (20.0-25.0) SXS (40.0-45.0) | NaOH (7.0-8.0) | Lambda carrageenan (20.0-25.0) | | | |
| 0.525% calcium hypochlorite | Acid Green 50 (3.0-5.0) | SDS (0.0-2.0) SXS (58.0-65.0) | NaOH (4.0-5.0) | Lambda carrageenan (30.0-35.0) | — | — | |
| 0.2% calcium hypochlorite | Acid Green 50 (3.0-5.0) | SDS (22.0-27.0) SXS (45.0-50.0) | NaOH (3.0-4.0) | Lambda carrageenan (15.0-22.0) | — | — | |
| 0.525% sodium dichloroiso-cyanurate | Acid Green 50 (4.0-5.0) | SDS (15.0-18.0) SXS (30.0-35.0) Surfynol 104S (5.0-8.0) | NaOH (20.0-28.0) Ca(OH)$_2$ (3.0-6.0) | Lambda carrageenan (10.0-18.0) | | | |
| 0.30% peracetic acid | FD&C Blue 1 (20.0-30.0) | — | NaOH (20.0-30.0) | | HTAB (33.0-50.0) | — | 4 |
| 0.20% chlorine dioxide | Thymolpthalein (15.0-20.0) | — | NaOH (6.0-10.0) | | Ethanol (70.0-80.0) | — | 36 |
| 7.5% hydrogen peroxide | Indigo carmine (7.0-10.0) | SDS (40.0-50.0) | NaOH (7.0-10.0) | | Copper (II) sulfate pentahydrate (40.0-45.0) | — | 34 |

Methods for Disinfecting a Surface

In embodiments, the disclosure also provides methods for disinfecting a surface by applying a coating of an aqueous solution comprising an oxidizing agent and a composition described herein to the surface and waiting for a period of time until the color of the solution has faded to clear, thereby disinfecting the surface.

In embodiments, the oxidizing agent is selected from the group consisting of sodium hypochlorite, calcium hypochlorite, sodium dichloroisocyanurate (NaDCC), hydrogen peroxide, chlorine dioxide, peracetic acid, benzalkonium chloride, alkyldimethylbenzylammonium chloride, quaternary ammonium compounds, phenols, and alcohols, such as ethanol and isopropyl alcohol.

In embodiments, the surface may be porous or nonporous surface. In embodiments, the surface may be concrete, steel, wood, ceramic, polypropylene, plastics, glass, metals, granite, etc. In embodiments, the surface may be a fabric.

In embodiments, the period of time is selected from 30 seconds to 30 minutes, preferably from about 30 seconds to 3 minutes, 30 seconds to 5 minutes, 5 minutes to 10 minutes, or 10 minutes to 15 minutes. In embodiments, the period of time is about 30 seconds or about 1, 2, 3, 5, 8, 10, 12, 15, or 30 minutes.

In embodiments, the composition is present in the aqueous solution in an amount of 0.5-5% w/v in 0.5% sodium or calcium hypochlorite, 1-5% w/v in 0.5% sodium dichloroisocyanurate, 0.3-1% w/v in 0.30% peracetic acid, 3-15% w/v in 0.2% chlorine dioxide, and 1-4.5% w/v in 7.5% hydrogen peroxide.

In embodiments, the coating is applied to the surface as a spray or mist.

In embodiments, the coating is applied in a manner suitable to achieve a layer of the solution on the surface that is about 1-3 millimeters (mm) thick.

In embodiments, the coating is applied in a manner suitable to achieve a layer of the solution on the surface that is about 3-6 millimeters (mm) thick.

The compositions and methods described here provide numerous advantages over prior compositions and methods for disinfecting surfaces. The compositions described here are adapted to provide different durations of color, both in solution in the bulk container, and after application to a surface. This feature provides a substantial advantage over typical colored disinfectant solutions. For example, an end-user may require a 3 minute color-fading time to indicate inactivation of a certain pathogen, but it would be a waste if an entire container of additive-enhanced disinfectant also faded in color after 3 minutes, limiting the color-fading application to a single use with a small volume.

In addition, the point of use methodology is another advantageous feature of the present compositions. For example, mixing an indicator composition as described here with a disinfectant solution immediately before use eliminates the need to maintain the color of the solution in a bulk container for extended periods of time, such as days, weeks, or even months or years, as is the case with color indicators added to the solution in a bulk container at the point of manufacture. In addition, formulating the compositions as a point of use additive allows the end user to enhance any conventional disinfectant without requiring the purchase of either a new disinfectant, or new equipment or supplies, as is the case with some other specialized disinfectants (e.g., e-misters). The compositions described here also dissolve rapidly in aqueous solutions (i.e., in less than about 30 seconds), making the process of preparing the disinfectant solution at the point of use simple and intuitive, such that it requires virtually no training. This means that the compositions and methods described here can readily be incorporated into current decontamination protocols.

In addition, the compositions described here are easy to transport and store, compared to bulk solutions, and they offer substantial cost savings compared to other colored disinfectant solutions. It is estimated that the cost per gallon of disinfectant solution treated with the compositions described here is from one tenth to one fiftieth the cost of a typical bulk colored solution. The powder form of the compositions described here is particularly advantageous for its portability. It is lightweight for transportation and reduces cost of deployment, especially in remote or low-resource areas. The powder form also has high stability, with a shelf life of at least 6 to 12 months, and extended to several years if stored in a sealed container away from light and heat.

Depending on the application at hand, other percentages of these components and other combinations of surfactants, alkaline builders, rheology modifiers, water-soluble dyes, ROS-generating catalysts and/or perfumes may be used without departing from the scope of the invention. Other disinfectant types and solutions may be used as well. The method of usage includes sprays and wipes, but other application forms may be used without deviating from the scope of the invention.

Of particular importance for real-world application, the composition of the point-of-use additive may be selected from the Environmental Protection Agency (EPA) Inert List, or such that the additive-enhanced disinfectant is not a significant irritant relative to the disinfectant alone, and such that the additive does not reduce the antimicrobial efficacy of the disinfectant.

EXAMPLES

The following non-limiting examples are provided to further illustrate embodiments of the invention disclosed herein. It will be appreciated by those of skill in the art that the techniques disclosed in the examples that follow represent approaches that have been found to function well in the practice of the invention and thus can be considered to constitute examples of modes for its practice. However, those of skill in the art will, in light of the present disclosure, appreciate that many changes can be made in the specific embodiments that are disclosed and still obtain a like or similar result without departing from the spirit and scope of the invention.

Example 1

Powdered compositions were made consisting of:

| | % Wt./Wt. | | | |
|---|---|---|---|---|
| Ingredient | Composition A | Composition B | Composition C | Composition D |
| FD&C Blue 1 | 1.18 | 2.33 | 4.55 | 8.70 |
| Surfactant (SDS) | 94.12 | 93.02 | 90.91 | 86.96 |
| Alkaline builder (NaOH) | 4.71 | 4.65 | 4.55 | 4.35 |

The procedure was to blend the ingredients and stir into 0.525% sodium hypochlorite diluted in water. 200 µl of the resulting mixtures was pipetted in quadruplets into separate wells of a 24-well plate. A spectrophotometer was used to measure absorbance (620 nm) 1, 2, 3, 5, 8, 12, 15, 20, and 30 minutes after the mixture was prepared. Reaction rates were averaged across the quadruplet wells and plotted against time.

When these formulas are mixed into 0.525% sodium hypochlorite diluted in water, the resulting mixtures are light to deep blue solutions. Compositions A, B, C, and D fade in 2, 5, 10, and 18 minutes when applied to a surface, respectively. All compositions are stable in color for 45 minutes when left in solution.

The purpose of this example is to show that the reaction rate of color fading is well modulated by adjusting the concentration of FD&C Blue 1 in the formula (FIG. 1).

Example 2

Powdered compositions were made consisting of:

| | % Wt./Wt. | | | |
|---|---|---|---|---|
| Ingredient | Composition A | Composition B | Composition C | Composition D |
| FD&C Blue 1 | 8.33 | 4.55 | 2.38 | 1.61 |
| Surfactant (SDS) | 83.33 | 90.91 | 95.24 | 96.77 |
| Alkaline builder (NaOH) | 8.33 | 4.55 | 2.38 | 1.61 |

The procedure was to blend the ingredients and stir into 0.525% sodium hypochlorite diluted in water. 200 µl of the resulting mixtures was pipetted in quadruplets into separate wells of a 24-well plate. A spectrophotometer was used to measure absorbance (620 nm) 1, 2, 3, 5, 8, 12, 15, 20, and 30 minutes after the mixture was prepared. Reaction rates were averaged across the quadruplet wells and plotted against time.

When these formulas are mixed into 0.525% sodium hypochlorite diluted in water, the resulting mixtures are deep blue solutions. Compositions A, B, C, and D fade in 8, 10, 12, and 15 minutes when applied to a surface, respectively. Compositions A and B are stable in color for 45 minutes when left in solution. Compositions C and D are stable in color for 70 minutes when left in solution.

Figure 2:
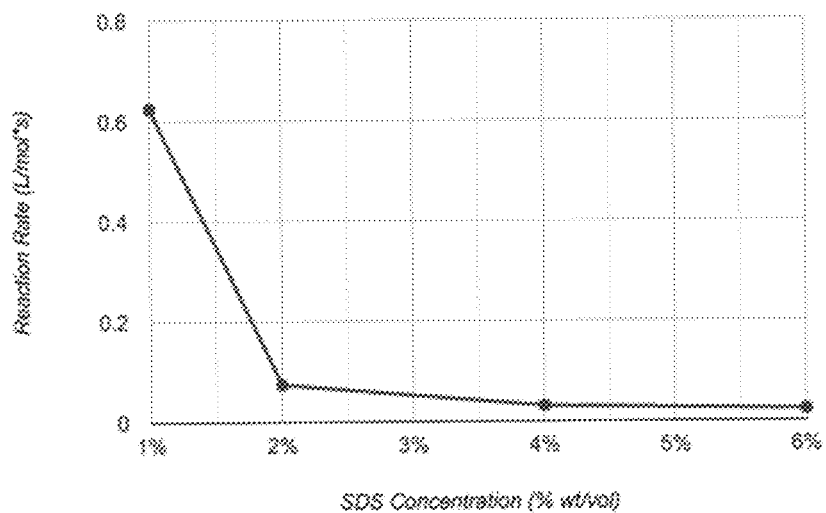
FIG. 2: Line graph representing the effect of changing the concentration of surfactant SDS on color fading reaction rate when a composition is added into 0.525% sodium hypochlorite. Reaction rate is obtained based on absorbance measurements over time.

The purpose of this example is to show that the reaction rate of color fading is well modulated by adjusting the concentration of sodium dodecyl sulfate (SDS) in the formula (FIG. 2). In addition, this example shows that a precise 20:1 ratio of surfactant to dye is sufficient to achieve color persistence, with larger ratios having less effect on slowing the reaction.

Example 3

Powdered compositions were made consisting of:

| | % Wt./Wt. | | | | |
|---|---|---|---|---|---|
| Ingredient | Comp. A | Comp. B | Comp. C | Comp. D | Comp. E |
| FD&C Blue 1 | 4.76 | 4.65 | 4.55 | 3.85 | 3.23 |
| Surfactant (SDS) | 95.24 | 93.02 | 90.91 | 76.92 | 64.52 |
| Alkaline builder (NaOH) | 0.00 | 2.33 | 4.55 | 19.23 | 32.26 |

The procedure was to blend the ingredients and stir into 0.525% sodium hypochlorite diluted in water. 200 µl of the resulting mixtures was pipetted in quadruplets into separate wells of a 24-well plate. A spectrophotometer was used to measure absorbance (620 nm) 1, 2, 3, 5, 8, 12, 15, 20, and 30 minutes after the mixture was prepared. Reaction rates were averaged across the quadruplet wells and plotted against time.

When these formulas are mixed into 0.525% sodium hypochlorite diluted in water, the resulting mixtures are deep blue solutions. Compositions A, B, C, D, and E fade in 2, 4, 10, 12, and 15 minutes when applied to a surface, respectively. Compositions A, B, C, D, and E are stable in color for 12, 20, 45, 60, and 70 minutes when left in solution, respectively.

Figure 3:
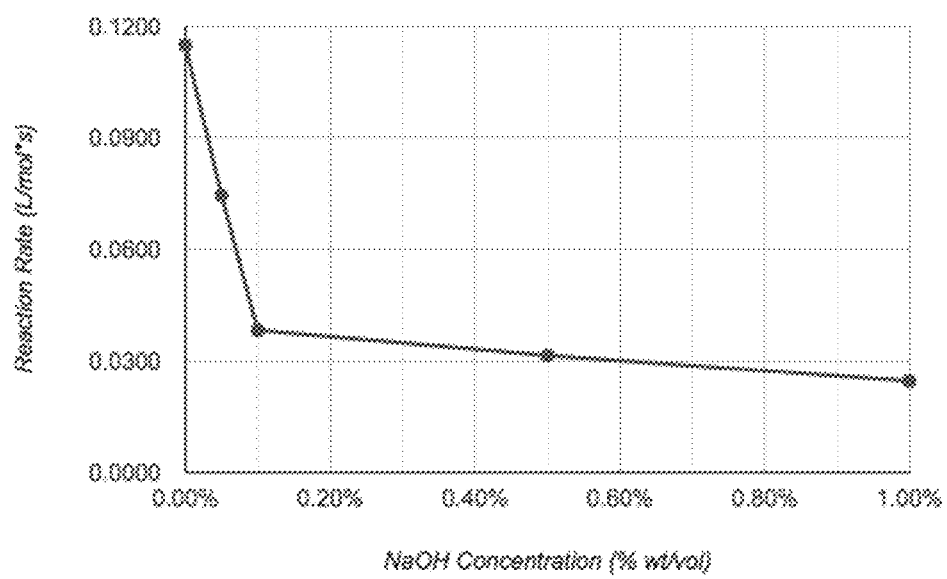
FIG. 3: Line graph representing the effect of changing the concentration of alkaline builder NaOH on color fading reaction rate when a composition is added into 0.525% sodium hypochlorite. Reaction rate is obtained based on absorbance measurements over time.

The purpose of this example is to show that the reaction rate of color fading is well modulated by adjusting the concentration of sodium hydroxide (NaOH) in the formula (FIG. 3). In addition, this example shows that a precise 1:1 ratio of NaOH to dye is sufficient to achieve color persistence, with larger ratios having less effect on slowing the reaction.

Example 4

Powdered compositions were made consisting of:

| | % Wt./Wt. | | |
|---|---|---|---|
| Ingredient | Composition A | Composition B | Composition C |
| FD&C Blue 1 | 40.00 | 33.33 | 25.00 |
| Catalyst (HTAB) | 20.00 | 33.33 | 50.00 |
| Alkaline builder (NaOH) | 40.00 | 33.33 | 25.00 |

The procedure was to blend the ingredients and stir into 0.30% peracetic acid diluted in water. 200 µl of the resulting mixtures was pipetted in quadruplets into separate wells of a 24-well plate. A spectrophotometer was used to measure absorbance (620 nm) 1, 2, 3, 5, 8, 12, 15, 20, and 30 minutes after the mixture was prepared. Reaction rates were averaged across the quadruplet wells and plotted against time.

When these formulas are mixed into 0.30% peracetic acid diluted in water, the resulting mixtures are deep blue solutions. Compositions A, B, and C fade in 10, 5, and 2 minutes when applied to a surface, respectively. Compositions A, B and C are stable in color for 50, 30, and 10 minutes when left in solution, respectively.

Figure 4:
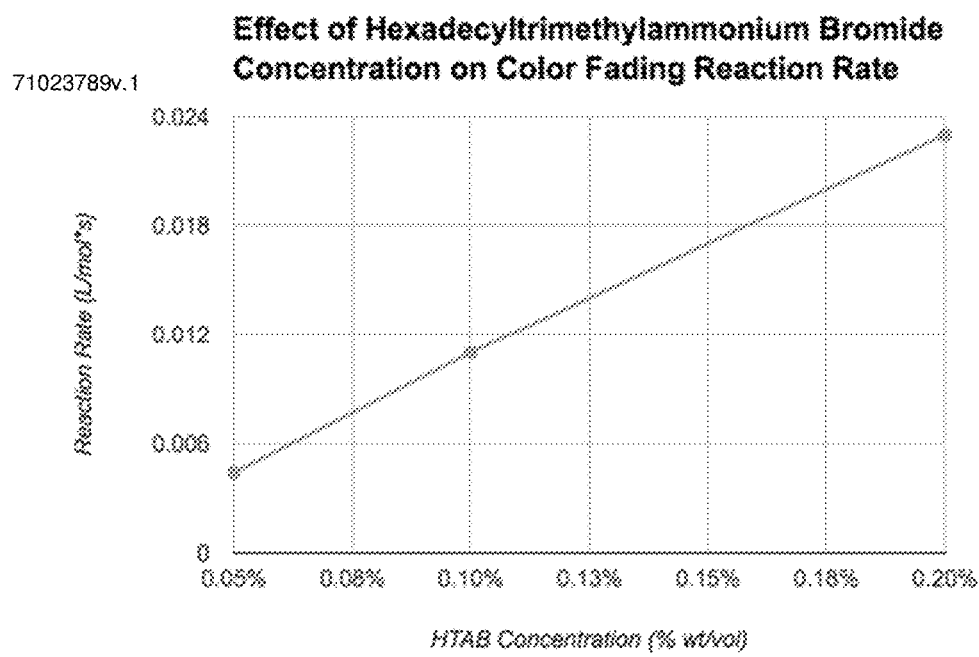
FIG. 4: Line graph representing the effect of changing the concentration of catalyst HTAB on color fading reaction rate when a composition is added into 0.3% peracetic acid. Reaction rate is obtained based on absorbance measurements over time.

The purpose of this example is to show that the reaction rate of color fading is well modulated by adjusting the concentration of hexadecyltrimethylammonium bromide (HTAB) in the formula (FIG. 4). HTAB functions as a catalyst within peracetic acid, and increasing its concentration increases the rate of the color fading reaction. One skilled in the art can appreciate that other catalysts may be used without deviating from the scope of the invention.

Example 5

A powdered composition consisting of:

| | % Wt./Wt. | | | | |
|---|---|---|---|---|---|
| Ingredient | Comp. A | Comp. B | Comp. C | Comp. D | Comp. E |
| Patent Blue V | 4.08 | 10.22 | 3.68 | 5.88 | 7.72 |
| Surfactant (SDS) | 81.63 | 73.3 | 92.11 | 85.56 | 88.80 |
| Alkaline builder (NaOH) | 14.29 | 16.48 | 4.21 | 8.56 | 3.47 |

When these formulas are mixed into 0.525% sodium hypochlorite or calcium hypochlorite diluted in water, the resulting mixtures are deep blue solutions. Compositions A, B, C, D, and E fade in 18, 30, 15, 20, and 25 minutes when applied to a surface, respectively. Compositions A, B, C, D, and E are stable in color for 130, 180, 140, 140, and 160 minutes when left in solution, respectively.

Example 6

A powdered composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 4.55 | 7.84 | 13.33 | 5.93 | 8.83 |
| Surfactant (SDS) | 90.91 | 86.27 | 75.56 | 90.91 | 88.34 |
| Alkaline builder (Ca(OH)$_2$) | 4.55 | 5.88 | 11.11 | 3.16 | 2.83 |

When these formulas are mixed into 0.525% sodium hypochlorite or calcium hypochlorite diluted in water, the resulting mixtures are bright blue solutions. Compositions A, B, C, D, and E fade in 6, 10, 18, 7, and 14 minutes when applied to a surface, respectively. Compositions A, B, C, D, and E are stable in color for 180, 150, 150, 180, and 160 minutes when left in solution, respectively.

Example 7

A powdered composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 2.33 | 5.13 | 10.85 | 5.03 | 3.97 |
| Surfactant (SXS) | 88.37 | 91.88 | 85.27 | 90.45 | 92.59 |
| Alkaline builder (NaOH) | 9.30 | 2.99 | 3.88 | 4.52 | 3.44 |

When these formulas are mixed into 0.525% sodium hypochlorite or calcium hypochlorite diluted in water, the resulting mixtures are deep blue solutions. Compositions A, B, C, D, and E fade in 10, 12, 12, 2, and 4 minutes when applied to a surface, respectively. Compositions A, B, C, D, and E are stable in color for 45, 50, 45, 20, and 25 minutes when left in solution, respectively.

Example 8

A powdered composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 19.35 | 10.81 | 7.50 | 15.90 | 8.42 |
| Surfactant (STS) | 64.52 | 81.08 | 87.50 | 81.27 | 87.54 |
| Alkaline builder (NaOH) | 16.13 | 8.11 | 5.00 | 2.83 | 4.04 |

When these formulas are mixed into 0.525% sodium hypochlorite or calcium hypochlorite diluted in water, the resulting mixtures are deep blue solutions. Compositions A, B, C, D, and E fade in 14, 8, 6, 12, and 6 minutes when applied to a surface, respectively. Compositions A, B, C, D, and E are stable in color for 17, 12, 9, 1, and 9 minutes when left in solution, respectively.

Example 9

A liquid composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 2.55 | 3.68 | 3.61 | 13.51 | 12.50 |
| Surfactant (SLES) | 94.39 | 91.91 | 82.33 | 83.01 | 56.25 |
| Alkaline builder (NaOH) | 3.06 | 4.41 | 14.06 | 3.47 | 31.25 |

When these formulas are mixed into 0.525% sodium hypochlorite or calcium hypochlorite diluted in water, the resulting mixtures are deep blue solutions. Compositions A, B, C, D, and E fade in 2, 4, 4, 27, and 25 minutes when applied to a surface, respectively. Compositions A, B, C, D, and E are stable in color for 10, 20, 20, 40, and 40 minutes when left in solution, respectively.

Example 10

A powdered composition consisting of:

| | % Wt./Wt. | | | | |
|---|---|---|---|---|---|
| Ingredient | Comp. A | Comp. B | Comp. C | Comp. D | Comp. E |
| FD&C Yellow 5 | 23.26 | 28.26 | 11.76 | 5.45 | 8.47 |
| Surfactant (SDS) | 69.77 | 67.39 | 78.43 | 83.64 | 84.75 |
| Alkaline builder (NaOH) | 6.98 | 4.35 | 9.80 | 10.91 | 6.78 |

The purpose of this example is to show that the compatibility of other colors of water-soluble and oxidizable dyes in the formula.

When these formulas are mixed into 0.525% sodium hypochlorite or calcium hypochlorite diluted in water, the resulting mixtures are yellow solutions. Compositions A, B, C, D, and E fade in 60, 80, 10, 1, and 6 seconds when applied to a surface, respectively. Compositions A, B, C, D, and E are stable in color for 23, 25, 16, 5, and 10 minutes when left in solution, respectively.

Example 11

A powdered composition consisting of:

| | % Wt./Wt. | | | | |
|---|---|---|---|---|---|
| Ingredient | Comp. A | Comp. B | Comp. C | Comp. D | Comp. E |
| Fast Green FCF | 8.70 | 2.91 | 6.05 | 21.93 | 4.19 |
| Surfactant (SDS) | 86.96 | 91.02 | 90.73 | 72.37 | 90.70 |
| Alkaline builder (NaOH) | 4.35 | 6.07 | 3.23 | 5.70 | 5.12 |

When these formulas are mixed into 0.525% sodium hypochlorite or calcium hypochlorite diluted in water, the resulting mixtures are green solutions. Compositions A, B, C, D, and E fade in 5, 1, 3, 17 and 4 minutes when applied to a surface, respectively. Compositions A, B, C, D, and E are stable in color for 45, 25, 37, 60, and 40 minutes when left in solution, respectively.

Example 12

A powdered composition consisting of:

| | % Wt./Wt. | | | | |
|---|---|---|---|---|---|
| Ingredient | Comp. A | Comp. B | Comp. C | Comp. D | Comp. E |
| Indigo Carmine | 27.12 | 33.90 | 42.62 | 41.67 | 33.33 |
| Surfactant (SDS) | 67.80 | 59.32 | 49.18 | 55.56 | 58.67 |
| Alkaline builder (NaOH) | 5.08 | 6.78 | 8.20 | 2.78 | 8.00 |

When these formulas are mixed into 0.525% sodium hypochlorite or and calcium hypochlorite diluted in water, the resulting mixtures are grey solutions. Compositions A, B, C, D, and E fade in 80, 100, 150, 150, and 120 seconds when applied to a surface, respectively. Compositions A, B, C, D, and E are stable in color for 15, 15, 25, 20, and 17 minutes when left in solution, respectively.

Example 13

A powdered composition consisting of:

| | % Wt./Wt. | | | | |
|---|---|---|---|---|---|
| Ingredient | Comp. A | Comp. B | Comp. C | Comp. D | Comp. E |
| Acid Blue 80 | 4.44 | 5.66 | 6.00 | 3.05 | 10.00 |
| Surfactant (SDS) | 80.00 | 85.34 | 70.00 | 90.95 | 82.50 |
| Alkaline builder (NaOH) | 15.56 | 9.00 | 24.00 | 6.00 | 7.50 |

When these formulas are mixed into 0.525% sodium hypochlorite or calcium hypochlorite diluted in water, the resulting mixtures are deep blue solutions. Compositions A, B, C, D, and E fade in 7, 9, 12, 9, and 9 minutes when applied to a surface, respectively. Compositions A, B, C, D, and E are stable in color for 180, 250, 480, 390 and 430 minutes when left in solution, respectively.

Example 14

A powdered composition consisting of:

| | % Wt./Wt. | | | | |
|---|---|---|---|---|---|
| Ingredient | Comp. A | Comp. B | Comp. C | Comp. D | Comp. E |
| Remazol Brilliant Blue R | 8.57 | 13.33 | 19.64 | 29.00 | 10.50 |
| Surfactant (SDS) | 85.70 | 77.78 | 71.43 | 50.67 | 69.00 |
| Alkaline builder (NaOH) | 5.73 | 8.89 | 8.93 | 20.33 | 21.50 |

When these formulas are mixed into 0.525% sodium hypochlorite or calcium hypochlorite diluted in water, the resulting mixtures are deep blue solutions. Compositions A, B, C, D, and E fade in 6, 9, 14, 12, and 13 minutes when applied to a surface, respectively. Compositions A, B, C, D, and E are stable in color for 120, 290, 430, 350, and 400 minutes when left in solution, respectively.

Example 15

A powdered composition consisting of:

| | % Wt./Wt. | | | | |
|---|---|---|---|---|---|
| Ingredient | Comp. A | Comp. B | Comp. C | Comp. D | Comp. E |
| Acid Green 25 | 2.11 | 4.00 | 11.11 | 5.94 | 13.60 |
| Surfactant (SDS) | 89.89 | 88.00 | 83.33 | 89.11 | 75.40 |
| Alkaline builder (NaOH) | 9.00 | 8.00 | 5.56 | 4.95 | 11.00 |

When these formulas are mixed into 0.525% sodium hypochlorite or calcium hypochlorite diluted in water, the resulting mixtures are deep blue solutions. Compositions A, B, C, D, and E fade in 5, 6, 10, 11, and 15 minutes when applied to a surface, respectively. Compositions A, B, C, D, and E are stable in color for 75, 110, 275, 300, and 340 minutes when left in solution, respectively.

Example 16

A powdered composition consisting of:

| | % Wt./Wt. | | | | |
|---|---|---|---|---|---|
| Ingredient | Comp. A | Comp. B | Comp. C | Comp. D | Comp. E |
| Crystal Violet Lactone | 31.25 | 9.30 | 4.17 | 12.47 | 6.15 |
| Surfactant (SDS) | 62.50 | 89.00 | 72.92 | 79.53 | 90.00 |
| Alkaline builder (NaOH) | 6.25 | 1.70 | 22.92 | 10.00 | 3.85 |

When these formulas are mixed into 0.525% sodium hypochlorite or calcium hypochlorite diluted in water, the resulting mixtures are deep blue solutions. Compositions A, B, C, D, and E fade in 2, 1, 0.5, 3, and 1 minutes when applied to a surface, respectively. Compositions A, B, C, D, and E are all stable in color for at least 6 hours when left in solution.

Example 17

A powdered composition consisting of:

| | % Wt./Wt. | | | | |
|---|---|---|---|---|---|
| Ingredient | Comp. A | Comp. B | Comp. C | Comp. D | Comp. E |
| Thymolphthalein | 4.76 | 17.28 | 30.91 | 28.58 | 34.88 |
| Surfactant (SDS) | 47.62 | 36.36 | 27.27 | 35.71 | 34.88 |
| Alkaline builder (NaOH) | 47.62 | 46.36 | 41.82 | 35.71 | 30.24 |

When these formulas are mixed into 0.525% sodium hypochlorite or calcium hypochlorite diluted in water, the resulting mixtures are deep violet solutions. Compositions A, B, C, D, and E fade in 3, 6, 12, 10, and 15 minutes when applied to a surface, respectively. Compositions A, B, C, D, and E are all stable in color for at least 6 hours when left in solution.

Example 18

A powdered composition consisting of:

| Ingredient | % Wt./Wt. | | | | |
|---|---|---|---|---|---|
| | Comp. A | Comp. B | Comp. C | Comp. D | Comp. E |
| Bromothymol Blue | 11.30 | 3.00 | 7.09 | 5.30 | 10.84 |
| Surfactant (SDS) | 69.35 | 86.45 | 70.92 | 81.70 | 78.32 |
| Alkaline builder (NaOH) | 19.35 | 10.55 | 21.99 | 13.00 | 10.84 |

When these formulas are mixed into 0.525% sodium hypochlorite or calcium hypochlorite diluted in water, the resulting mixtures are deep blue solutions. Compositions A, B, C, D, and E fade in 0.5, 2, 1, 2, and 1 minutes when applied to a surface, respectively. Compositions A, B, C, D, and E are all stable in color for at least 6 hours when left in solution.

Example 19

A powdered composition consisting of:

| Ingredient | % Wt./Wt. | | | | |
|---|---|---|---|---|---|
| | Comp. A | Comp. B | Comp. C | Comp. D | Comp. E |
| FD&C Blue 1 | 6.38 | 9.43 | 21.15 | 4.35 | 22.08 |
| Surfactant (SDS) | 85.11 | 81.13 | 57.69 | 89.96 | 58.44 |
| Alkaline builder (KOH) | 8.51 | 9.43 | 21.15 | 5.70 | 19.48 |

When these formulas are mixed into 0.525% sodium hypochlorite or calcium hypochlorite diluted in water, the resulting mixtures are deep blue solutions. Compositions A, B, C, D, and E fade in 13, 20, 28, 10, and 27 minutes when applied to a surface, respectively. Compositions A, B, C, D, and E are stable in color for 50, 60, 70, 45, and 70 minutes when left in solution, respectively.

Example 20

A powdered composition consisting of:

| Ingredient | % Wt./Wt. | | | | |
|---|---|---|---|---|---|
| | Comp. A | Comp. B | Comp. C | Comp. D | Comp. E |
| FDC&C Blue 1 | 5.00 | 2.63 | 11.19 | 17.24 | 5.35 |
| Surfactant (SDS) | 75.00 | 65.79 | 57.84 | 25.86 | 64.24 |
| Alkaline builder (NaOH) | 5.00 | 5.26 | 2.99 | 17.24 | 10.71 |
| Sodium alginate | 15.00 | 26.32 | 27.99 | 39.66 | 19.70 |

The purpose of this example is to show that the addition of a rheology modifier like sodium alginate both thickens the solution and improves color persistence by slowing the color fading reaction. One skilled in the art can appreciate that other rheology modifiers may be used without deviating from the scope of the invention.

When these formulas are mixed into 0.525% sodium hypochlorite or calcium hypochlorite diluted in water, the resulting mixtures are deep blue solutions. Compositions A, B, C, D, and E fade in 5, 3, 12, 15, and 4 minutes when applied to a surface, respectively. Compositions A, B, C, D, and E are stable in color for 30, 25, 35, 37, and 28 minutes when left in solution, respectively.

Example 21

A powdered composition consisting of:

| Ingredient | % Wt./Wt. | | | | |
|---|---|---|---|---|---|
| | Comp. A | Comp. B | Comp. C | Comp. D | Comp. E |
| FD&C Blue 1 | 5.36 | 3.57 | 5.45 | 6.85 | 6.19 |
| Surfactant (SDS) | 78.90 | 62.50 | 54.55 | 34.25 | 36.08 |
| Alkaline builder (NaOH) | 5.26 | 7.14 | 3.64 | 4.11 | 6.19 |
| Lambda Carrageenan | 10.50 | 26.79 | 36.36 | 54.79 | 51.55 |

When these formulas are mixed into 0.525% sodium hypochlorite or calcium hypochlorite diluted in water, the resulting mixtures are deep blue solutions. Compositions A, B, C, D, and E fade in 25, 15, 20, 28, and 27 minutes when applied to a surface, respectively. Compositions A, B, C, D, and E are stable in color for 45, 35, 40, 35, and 40 minutes when left in solution, respectively.

Example 22

A powdered composition consisting of:

| Ingredient | % Wt./Wt. | | | | |
|---|---|---|---|---|---|
| | Comp. A | Comp. B | Comp. C | Comp. D | Comp. E |
| Acid Green 50 | 6.67 | 1.69 | 8.68 | 21.47 | 6.02 |
| Surfactant (SDS) | 13.33 | 72.88 | 55.47 | 60.21 | 19.28 |
| Alkaline builder (NaOH) | 33.33 | 8.47 | 13.21 | 2.62 | 14.46 |
| Guar Gum | 46.67 | 16.95 | 22.64 | 15.71 | 60.24 |

When these formulas are mixed into 0.525% sodium dichloroisocyanurate diluted in water, the resulting mixtures are deep blue solutions. Compositions A, B, C, D, and E fade in 7, 1, 10, 25, and 6 minutes when applied to a surface, respectively. Compositions A, B, C, D, and E are stable in color for 240, 100, 250, 280, and 200 minutes when left in solution, respectively.

Example 23

A powdered composition consisting of:

| Ingredient | % Wt./Wt. | | | | |
|---|---|---|---|---|---|
| | Comp. A | Comp. B | Comp. C | Comp. D | Comp. E |
| Acid Green 50 | 6.67 | 7.14 | 4.41 | 6.17 | 6.19 |
| Surfactant (SDS) | 33.33 | 62.50 | 44.12 | 40.74 | 36.08 |
| Alkaline builder (NaOH) | 26.67 | 7.14 | 7.35 | 3.70 | 6.19 |
| Locust Bean | 33.33 | 23.21 | 44.12 | 49.38 | 51.55 |

When these formulas are mixed into 0.525% sodium dichloroisocyanurate diluted in water, the resulting mixtures are deep blue solutions. Compositions A, B, C, D, and E fade in 10, 12, 5, 10, and 11 minutes when applied to a surface, respectively. Compositions A, B, C, D, and E are stable in color for 250, 300, 200, 180, and 170 minutes when left in solution, respectively.

Example 24

A powdered composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 2.70 | 2.50 | 6.67 | 9.02 | 8.92 |
| Surfactant (SDS) | 40.50 | 43.75 | 47.22 | 47.59 | 44.05 |
| Sodium alginate | 2.70 | 10.25 | 4.73 | 10.00 | 3.81 |
| Lambda carrageenan | 6.80 | 12.25 | 5.27 | 10.01 | 6.18 |
| Alkaline builder (NaOH) | 6.80 | 6.25 | 5.56 | 7.59 | 13.51 |
| Fumed Silica | 40.50 | 25.00 | 30.56 | 15.79 | 23.51 |

When these formulas are mixed into 0.525% sodium hypochlorite or calcium hypochlorite diluted in water, the resulting mixtures are deep blue solutions. Compositions A, B, C, D, and E fade in 12, 11, 20, 27, and 23 minutes when applied to a surface, respectively. Compositions A, B, C, D, and E are stable in color for 30, 35, 40, 45, and 40 minutes when left in solution, respectively.

Example 25

A powdered composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 2.82 | 10.10 | 3.50 | 1.00 | 5.55 |
| Surfactant (SDS) | 66.10 | 70.71 | 81.65 | 75.98 | 60.69 |
| Alkaline builder (NaOH) | 16.95 | 6.57 | 4.85 | 5.55 | 6.59 |
| Sodium Polyacrylate | 14.12 | 12.63 | 10.00 | 17.47 | 27.17 |

When these formulas are mixed into 0.525% sodium hypochlorite or calcium hypochlorite diluted in water, the resulting mixtures are deep blue solutions. Compositions A, B, C, D, and E fade in 17, 40, 18, 7, and 25 minutes when applied to a surface, respectively. Compositions A, B, C, D, and E are stable in color for 180, 240, 120, 130, and 200 minutes when left in solution, respectively.

Example 26

A powdered composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 34.41 | 16.25 | 16.71 | 5.80 | 36.23 |
| Surfactant (SDS) | 42.51 | 72.20 | 71.60 | 43.48 | 21.74 |
| Alkaline builder (NaOH) | 14.84 | 0.72 | 0.95 | 21.74 | 3.99 |
| Potassium Nitrate | 8.24 | 10.83 | 10.74 | 28.99 | 38.04 |

When these formulas are mixed into 0.525% sodium hypochlorite or calcium hypochlorite diluted in water, the resulting mixtures are deep blue solutions. Compositions A, B, C, D, and E fade in 25, 15, 13, 10, and 12 minutes when applied to a surface, respectively. Compositions A, B, C, D, and E are stable in color for 35, 45, 50, 40, and 30 minutes when left in solution, respectively.

The purpose of this example is to show that oxidizing agents like potassium nitrate can be included in the formula to modulate the reaction rate of dye oxidation. One skilled in the art can appreciate that other oxidizing agents may be used without deviating from the scope of the invention.

Example 27

A powdered composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 7.41 | 11.76 | 7.50 | 9.26 | 9.23 |
| Surfactant (SDS) | 74.07 | 73.54 | 67.50 | 55.56 | 52.31 |
| Alkaline builder (NaOH) | 11.11 | 5.88 | 12.50 | 16.67 | 15.38 |
| Sodium Nitrite | 7.41 | 8.82 | 12.50 | 18.53 | 23.08 |

When these formulas are mixed into 0.525% sodium hypochlorite or calcium hypochlorite diluted in water, the resulting mixtures are deep blue solutions. Compositions A, B, C, D, and E fade in 15, 13, 13, 14, and 10 minutes when applied to a surface, respectively. Compositions A, B, C, D, and E are stable in color for 50, 45, 40, 40, and 40 minutes when left in solution, respectively.

Example 28

A powdered composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 3.51 | 7.95 | 6.00 | 7.24 | 12.37 |
| Surfactant (SDS) | 58.65 | 74.10 | 50.88 | 61.72 | 53.44 |
| Alkaline builder (NaOH) | 10.81 | 5.13 | 15.63 | 12.64 | 17.09 |
| Citric Acid | 27.03 | 12.82 | 27.50 | 18.39 | 17.09 |

When these formulas are mixed into 0.525% sodium hypochlorite or calcium hypochlorite diluted in water, the resulting mixtures are deep blue solutions. Compositions A, B, C, D, and E fade in 2, 6, 4, 6, and 8 minutes when applied to a surface, respectively. Compositions A, B, C, D, and E are stable in color for 35, 30, 32, 37, and 42 minutes when left in solution, respectively.

The purpose of this example is to show that perfumes like citric acid can be included in the formula to modulate the pH of the solution and thereby alter the reaction rate of color fading. One skilled in the art can appreciate that other perfumes may be used without deviating from the scope of the invention.

Example 29

A powdered composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 4.11 | 4.11 | 7.94 | 5.14 | 3.61 |
| Surfactant (SDS) | 13.70 | 13.70 | 26.19 | 38.99 | 51.02 |
| Sodium alginate | 13.70 | 27.40 | 28.62 | 9.33 | 15.46 |
| Sodium carbonate | 41.10 | 41.10 | 21.38 | 1.66 | 11.54 |
| Sodium xylene sulfonate | 27.40 | 54.80 | 15.87 | 45.87 | 18.37 |

When these formulas are mixed into 0.525% sodium hypochlorite or calcium hypochlorite diluted in water, the resulting mixtures are deep blue solutions. Compositions A, B, C, D, and E fade in 15, 20, 27, 17, and 11 minutes when applied to a surface, respectively. Compositions A, B, C, D, and E are stable in color for 27, 35, 40, 60, and 45 minutes when left in solution, respectively.

Example 30

A liquid composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 11.11 | 12.32 | 26.19 | 5 | 20.88 |
| DOWFAX 2A1 | 69.91 | 82.27 | 57.14 | 87.5 | 63.17 |
| Alkaline builder (NaOH) | 18.98 | 5.41 | 16.67 | 7.5 | 15.95 |

When these formulas are mixed into 0.525% sodium hypochlorite or calcium hypochlorite diluted in water, the resulting mixtures are deep blue solutions. Compositions A, B, C, D, and E fade in 10, 12, 20, 8, and 18 minutes when applied to a surface, respectively. Compositions A, B, C, D, and E are stable in color for 120, 80, 240, 75, and 180 minutes when left in solution, respectively.

Example 31

A powdered composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 4.76 | 13.28 | 12.66 | 6.03 | 5.96 |
| Surfactant (SDS) | 57.82 | 73.80 | 65.50 | 62.38 | 55.74 |
| Alkaline builder (NaOH) | 34.01 | 3.69 | 15.28 | 22.54 | 11.70 |
| Titanium Dioxide | 3.40 | 9.23 | 6.55 | 19.05 | 26.60 |

When these formulas are mixed into 0.525% sodium hypochlorite or calcium hypochlorite diluted in water, the resulting mixtures are deep blue solutions. Compositions A, B, C, D, and E fade in 4, 12, 10, 8, and 7 minutes when applied to a surface, respectively. Compositions A, B, C, D, and E are stable in color for 30, 60, 50, 45, and 40 minutes when left in solution, respectively.

The purpose of this example is to show that photocatalysts like titanium dioxide can be included in the formula to modulate the reaction rate of dye oxidation. One skilled in the art can appreciate that other photocatalysts may be used without deviating from the scope of the invention.

Example 32

A powdered composition consisting of:

| | % Wt./Wt. | | | | |
|---|---|---|---|---|---|
| Ingredient | Comp. A | Comp. B | Comp. C | Comp. D | Comp. E |
| Methylene Blue | 13.33 | 7.69 | 25 | 27.27 | 25.24 |
| Surfactant (SDS) | 73.17 | 76.92 | 68.18 | 63.64 | 71.31 |
| Alkaline builder (NaOH) | 13.5 | 15.38 | 6.82 | 9.09 | 3.45 |

When these formulas are mixed into 0.525% sodium hypochlorite or calcium hypochlorite diluted in water, the resulting mixtures are deep blue solutions. Compositions A, B, C, D, and E fade in 18, 15, 15, 13, and 4 minutes when applied to a surface, respectively. Compositions A, B, C, D, and E are stable in color for 200, 240, 120, 160, and 60 minutes when left in solution, respectively.

Example 33

A powdered composition consisting of:

| | % Wt./Wt. | | | | |
|---|---|---|---|---|---|
| Ingredient | Comp. A | Comp. B | Comp. C | Comp. D | Comp. E |
| RD&C Red 2 | 19.08 | 20.15 | 22.87 | 30.18 | 35.15 |
| Surfactant (SDS) | 76.34 | 68.91 | 56.61 | 39.61 | 28.87 |
| Alkaline builder (NaOH) | 4.58 | 10.94 | 20.52 | 30.21 | 35.98 |

When these formulas are mixed into 0.525% sodium hypochlorite or calcium hypochlorite diluted in water, the resulting mixtures are red solutions. Compositions A, B, C, D, and E fade in 1, 3, 5, 8, and 12 minutes when applied to a surface, respectively. Compositions A, B, C, D, and E are stable in color for 2, 10, 20, 35, and 40 minutes when left in solution, respectively.

Example 34

A powdered composition consisting of:

| | % Wt./Wt. | | | | |
|---|---|---|---|---|---|
| Ingredient | Comp. A | Comp. B | Comp. C | Comp. D | Comp. E |
| Indigo Carmine | 7.41 | 11.43 | 20.00 | 20.27 | 17.65 |
| Surfactant (SDS) | 74.07 | 57.14 | 50.00 | 47.30 | 47.06 |
| Alkaline builder (NaOH) | 11.11 | 17.14 | 10.00 | 12.16 | 11.76 |
| Copper (II) sulfate pentahydrate | 7.41 | 14.29 | 20.00 | 20.27 | 23.53 |

When these formulas are mixed into 7.5% hydrogen peroxide diluted in water, the resulting mixtures are light blue solutions. Compositions A, B, C, D, and E fade in 3, 5, 12, 15, and 16 minutes when applied to a surface, respectively. Compositions A, B, C, D, and E are stable in color for 20, 25, 30, 35, and 38 minutes when left in solution, respectively.

Example 35

A powdered composition consisting of:

| Ingredient | % Wt./Wt. | | | | |
|---|---|---|---|---|---|
| | Comp. A | Comp. B | Comp. C | Comp. D | Comp. E |
| Indigo Carmine | 7.25 | 6.90 | 16.95 | 9.09 | 20.00 |
| Surfactant (SDS) | 28.99 | 34.48 | 35.59 | 6.06 | 47.50 |
| Alkaline builder (NaOH) | 5.80 | 6.90 | 5.08 | 30.30 | 25.00 |
| Iron (III) nitrate nonahydrate | 57.97 | 51.72 | 42.37 | 54.55 | 7.50 |

When these formulas are mixed into 7.5% hydrogen peroxide diluted in water, the resulting mixtures are deep blue solutions. Compositions A, B, C, D, and E fade in 5, 3, 10, 6, and 12 minutes when applied to a surface, respectively. Compositions A, B, C, D, and E are stable in color for 25, 20, 28, 23, and 30 minutes when left in solution, respectively.

Example 36

A liquid composition consisting of:

| Ingredient | % Wt./Wt. | | | | |
|---|---|---|---|---|---|
| | Comp. A | Comp. B | Comp. C | Comp. D | Comp. E |
| Thymolpthalein | 2.86 | 3.74 | 1.42 | 7.33 | 6.86 |
| Water | 95.24 | 93.46 | 94.89 | 88.99 | 91.43 |
| Alkaline builder (NaOH) | 1.90 | 2.80 | 3.69 | 3.68 | 1.71 |

When these formulas are mixed into 0.2% chlorine dioxide diluted in water, the resulting mixtures are deep violet solutions. Compositions A, B, C, D, and E fade in 5, 15, 7, 27, and 15 minutes when applied to a surface, respectively. Compositions A, B, C, D, and E are stable in color for at least 6 hours when left in solution.

Example 37

A powdered composition consisting of:

| Ingredient | % Wt./Wt. | | | | |
|---|---|---|---|---|---|
| | Comp. A | Comp. B | Comp. C | Comp. D | Comp. E |
| FD&C Blue 1 | 8.00 | 10.00 | 10.94 | 6.33 | 8.16 |
| Surfactant (SDS) | 40.00 | 38.00 | 42.19 | 44.30 | 40.82 |
| Alkaline builder (NaOH) | 12.00 | 12.00 | 7.81 | 11.39 | 10.20 |
| Surfactant (SXS) | 40.00 | 40.00 | 39.06 | 37.97 | 40.82 |

When these formulas are mixed into 0.525% sodium hypochlorite or calcium hypochlorite diluted in water, the resulting mixtures are deep blue solutions. Compositions A, B, C, D, and E fade in 10, 12, 12, 7, and 10 minutes when applied to a surface, respectively. Compositions A, B, C, D, and E are stable in color for 50, 60, 55, 50, and 50 minutes when left in solution, respectively.

Example 38

A powdered composition consisting of:

| Ingredient | % Wt./Wt. | | | | |
|---|---|---|---|---|---|
| | Comp. A | Comp. B | Comp. C | Comp. D | Comp. E |
| FD&C Blue 1 | 7.41 | 5.80 | 13.43 | 6.49 | 1.33 |
| Surfactant (SDS) | 44.44 | 28.99 | 40.30 | 40.26 | 53.33 |
| Alkaline builder (KOH) | 11.11 | 7.25 | 8.96 | 11.69 | 8.00 |
| Surfactant (STS) | 37.04 | 57.97 | 37.31 | 41.56 | 37.33 |

When these formulas are mixed into 0.525% sodium hypochlorite or calcium hypochlorite diluted in water, the resulting mixtures are deep blue solutions. Compositions A, B, C, D, and E fade in 10, 5, 17, 7, and 2 minutes when applied to a surface, respectively. Compositions A, B, C, D, and E are stable in color for 50, 40, 70, 45, and 35 minutes when left in solution, respectively.

Example 39

A powdered composition consisting of:

| Ingredient | % Wt./Wt. | | | | |
|---|---|---|---|---|---|
| | Comp. A | Comp. B | Comp. C | Comp. D | Comp. E |
| FD&C Blue 1 | 8.00 | 1.61 | 14.06 | 20.69 | 25.32 |
| Surfactant (SDS) | 40.00 | 40.32 | 62.50 | 39.66 | 5.06 |
| Alkaline builder (NaOH) | 12.00 | 9.68 | 7.81 | 13.79 | 18.99 |
| DOWFAX 2A1 | 40.00 | 48.39 | 15.63 | 25.86 | 50.63 |

When these formulas are mixed into 0.525% sodium hypochlorite or calcium hypochlorite diluted in water, the resulting mixtures are deep blue solutions. Compositions A, B, C, D, and E fade in 8, 2, 15, 18, and 10 minutes when applied to a surface, respectively. Compositions A, B, C, D, and E are stable in color for 75, 40, 120, 200, and 90 minutes when left in solution, respectively.

Example 40

A powdered composition consisting of:

| Ingredient | % Wt./Wt. | | | | |
|---|---|---|---|---|---|
| | Comp. A | Comp. B | Comp. C | Comp. D | Comp. E |
| FD&C Blue 1 | 15.38 | 7.35 | 12.07 | 22.95 | 3.08 |
| Surfactant (SDS) | 51.28 | 66.18 | 60.34 | 50.82 | 61.54 |
| Alkaline builder (NaOH) | 17.95 | 8.82 | 15.52 | 21.31 | 23.08 |
| Acid Green 25 | 15.38 | 17.65 | 12.07 | 4.92 | 12.31 |

When these formulas are mixed into 0.525% sodium hypochlorite or calcium hypochlorite diluted in water, the resulting mixtures are deep blue solutions. Compositions A, B, C, D, and E fade in 10, 15, 12, 13, and 11 minutes when applied to a surface, respectively. Compositions A, B, C, D, and E are stable in color for 80, 95, 90, 90, and 90 minutes when left in solution, respectively.

Example 41

A powdered composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 6.45 | 6.06 | 13.85 | 6.94 | 8.00 |
| Surfactant (SDS) | 64.52 | 68.18 | 53.85 | 43.06 | 40.00 |
| Alkaline builder (NaOH) | 9.68 | 15.15 | 7.69 | 15.28 | 15.00 |
| Citric Acid | 6.45 | 6.06 | 15.38 | 20.83 | 17.00 |
| Surfynol 104S | 12.90 | 4.55 | 9.23 | 13.89 | 20.00 |

When these formulas are mixed into 0.525% sodium hypochlorite or calcium hypochlorite diluted in water, the resulting mixtures are deep blue solutions. Compositions A, B, C, D, and E fade in 7, 7, 15, 8, and 19 minutes when applied to a surface, respectively. Compositions A, B, C, D, and E are stable in color for 50, 50, 70, 45, and 60 minutes when left in solution, respectively.

Example 42

A liquid composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 0.75 | 1.00 | 1.25 | 1.50 | 1.50 |
| Surfactant (SXS) | 0.50 | 0.35 | 0.50 | 0.25 | 0.00 |
| Surfactant (SDS) | 0.00 | 0.30 | 0.25 | 0.50 | 0.75 |
| Water | 98.75 | 98.35 | 98.00 | 97.75 | 97.75 |

When these formulas are mixed into 0.525% sodium hypochlorite or calcium hypochlorite diluted in water, the resulting mixtures are blue solutions. Compositions A, B, C, D, and E fade in 30, 35, 40, 35, and 35 minutes when applied to a surface, respectively. Compositions A, B, C, D, and E are stable in color for 210, 220, 240, 220, and 220 minutes when left in solution, respectively. When compositions A, B, C, D and E are applied directly onto a wipe impregnated with 0.55% or 0.65% sodium hypochlorite, upon wiping a surface, a blue trace is left behind that fades away in 2, 3, 2, 3, and 3 minutes.

Example 43

A liquid composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 0.75 | 1.00 | 1.25 | 1.50 | 1.50 |
| Alkaline builder (NaOH) | 0.50 | 0.75 | 1.00 | 1.00 | 1.00 |
| Surfactant (SDS) | 0.00 | 0.25 | 0.35 | 0.50 | 0.75 |
| Water | 98.75 | 98.00 | 97.40 | 97.00 | 96.75 |

When these formulas are mixed into 0.525% sodium hypochlorite or calcium hypochlorite diluted in water, the resulting mixtures are blue solutions. Compositions A, B, C, D, and E fade in 40, 45, 50, 55, and 65 minutes when applied to a surface, respectively. Compositions A, B, C, D, and E are stable in color for 240, 260, 280, 300, and 310 minutes when left in solution, respectively. When compositions A, B, C, D and E are applied directly onto a wipe impregnated with 0.55% or 0.65% sodium hypochlorite, upon wiping a surface, a blue trace is left behind that fades away in 3, 3, 3, 4, and 4 minutes.

Example 44

A liquid composition consisting of:

| | % Wt./Wt. | | | | |
|---|---|---|---|---|---|
| Ingredient | Comp. A | Comp. B | Comp. C | Comp. D | Comp. E |
| FD&C Blue 1 | 0.75 | 1.00 | 1.25 | 1.50 | 1.50 |
| Alkaline builder (LiOH) | 0.50 | 0.75 | 1.00 | 1.00 | 1.00 |
| Surfactant (SDS) | 0.00 | 0.25 | 0.35 | 0.50 | 0.75 |
| Water | 98.75 | 98.00 | 97.40 | 97.00 | 96.75 |

When these formulas are mixed into 0.525% sodium hypochlorite or calcium hypochlorite diluted in water, the resulting mixtures are blue solutions. Compositions A, B, C, D, and E fade in 35, 45, 45, 50, and 65 minutes when applied to a surface, respectively. Compositions A, B, C, D, and E are stable in color for 200, 220, 240, 260, and 270 minutes when left in solution, respectively. When compositions A, B, C, D and E are applied directly onto a wipe imbued with 0.525% sodium hypochlorite, upon wiping a surface, a blue trace is left behind that fades away in 3, 3, 3, 4, and 4 minutes.

Example 45

A liquid composition consisting of:

| | % Wt./Wt. | | | | |
|---|---|---|---|---|---|
| Ingredient | Comp. A | Comp. B | Comp. C | Comp. D | Comp. E |
| Acid Green 50 | 0.75 | 1.00 | 1.25 | 1.50 | 1.50 |
| Surfactant (SXS) | 0.50 | 0.35 | 0.50 | 0.25 | 0.00 |
| Surfactant (SDS) | 0.00 | 0.30 | 0.25 | 0.50 | 0.75 |
| Water | 98.75 | 98.35 | 98.00 | 97.75 | 97.75 |

When these formulas are mixed into 0.525% sodium hypochlorite or calcium hypochlorite diluted in water, the resulting mixtures are blue solutions. Compositions A, B, C, D, and E fade in 35, 35, 40, 45, and 35 minutes when applied to a surface, respectively. Compositions A, B, C, D, and E are stable in color for 210, 210, 250, 260, and 220 minutes when left in solution, respectively. When compositions A, B, C, D and E are applied directly onto a wipe impregnated with 0.55% or 0.65% sodium hypochlorite, upon wiping a surface, a blue trace is left behind that fades away in 1, 2, 1, 2, and 3 minutes.

Example 46

A liquid composition consisting of:

| Ingredient | % Wt./Wt. | | | | |
|---|---|---|---|---|---|
| | Comp. A | Comp. B | Comp. C | Comp. D | Comp. E |
| FD&C Blue 1 | 0.50 | 0.75 | 1.25 | 1.50 | 2.50 |
| Surfactant (SXS) | 0.25 | 0.35 | 0.50 | 0.75 | 1.00 |
| Lambda Carrageenan | 0.00 | 0.30 | 0.25 | 0.35 | 0.50 |
| Water | 99.25 | 98.60 | 98.00 | 97.40 | 96.00 |

When these formulas are mixed into 0.525% sodium hypochlorite or calcium hypochlorite diluted in water, the resulting mixtures are blue solutions. Compositions A, B, C, D, and E fade in 25, 30, 40, 45, and 45 minutes when applied to a surface, respectively. Compositions A, B, C, D, and E are stable in color for 180, 200, 230, 240, and 220 minutes when left in solution, respectively. When compositions A, B, C, D and E are applied directly onto a wipe impregnated with 0.55% or 0.65% sodium hypochlorite, upon wiping a surface, a blue trace is left behind that fades away in 1, 2, 3, 4, and 5 minutes.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A colored aqueous solution of 0.1-2% sodium hypochlorite or calcium hypochlorite comprising
    at least one oxidizable water-soluble pigment,
    a surfactant selected from the group consisting of sodium dodecyl sulfate (SDS), sodium xylene sulfonate (SXS), sodium laureth sulfate (SLES), sodium myreth sulfate (SMS), sodium cholate, an acetylenic diol, alkyldiphenyloxide disulfonate, and sodium toluene sulfonate (STS), and mixtures thereof,
    an alkaline builder selected from the group consisting of sodium hydroxide (NaOH), calcium hydroxide (Ca(OH)$_2$), potassium hydroxide (KOH), and lithium hydroxide (LiOH), and mixtures thereof, and
    an optional rheology modifier selected from the group consisting of sodium alginate, glycerol, guar gum, dextran, cellulose, carrageenan (lambda, iota, kappa), sodium carbonate, fumed silica, alkali swellable emulsions, hydrophobically modified alkali swellable emulsions, hydrophobically-modified polyurethanes, and sodium polyacrylate, and mixtures thereof,
    wherein the color is stable in the colored aqueous solution of 0.1-2% sodium hypochlorite or calcium hypochlorite for from 10 to 20 minutes and fades to clear when the solution is applied as a spray or film to a surface.
2. The colored aqueous solution of claim 1, wherein the aqueous solution is 0.2-0.5% sodium hypochlorite or calcium hypochlorite.
3. The colored aqueous solution of claim 1, wherein the at least one oxidizable water-soluble pigment is FD&C Blue 1.
4. The colored aqueous solution of claim 3, wherein the total amount of oxidizable water-soluble pigment is from 0.5-2% w/v.
5. The colored aqueous solution of claim 1, wherein the at least one surfactant is selected from SDS, SXS, and mixtures thereof.
6. The colored aqueous solution of claim 5, wherein the total amount of surfactant is from 0.5-1.5% w/v.
7. The colored aqueous solution of claim 1, wherein the alkaline builder is selected from NaOH and KOH.
8. The colored aqueous solution of claim 7, wherein the total amount of alkaline builder is from 0.5-2% w/v.
9. The colored aqueous solution of claim 1, wherein the composition contains at least one rheology modifier selected from sodium alginate and lambda carrageenan, and mixtures thereof.
10. The colored aqueous solution of claim 9, wherein the total amount of rheology modifier is from 0.1-1% w/v.
11. The colored aqueous solution of claim 1, wherein the at least one oxidizable water-soluble pigment is selected from the group consisting of FD&C Blue, Acid Green, Patent Blue, FD&C Yellow, Fast Green FCF, Indigo Carmine, Acid Blue, Remazol Brilliant Blue, Coomassie Brilliant Blue, Methylene Blue, RD&C Red, and mixtures thereof.
12. The colored aqueous solution of claim 1, wherein the at least one oxidizable water-soluble pigment is selected from the group consisting of FD&C Blue, Acid Green, Patent Blue, FD&C Yellow, Fast Green FCF, Acid Blue, Remazol Brilliant Blue, Methylene Blue, RD&C Red, and mixtures thereof.
13. The colored aqueous solution of claim 12, wherein the at least one oxidizable water-soluble pigment is Acid Green or FD&C Blue.
14. The colored aqueous solution of claim 12, wherein the Acid Green is selected from Acid Green 25 and Acid Green 50.
15. The colored aqueous solution of claim 1, wherein the color fades to clear within a predetermined period of time of from 2 to 5 minutes when the solution is applied as a spray or film to a surface.
16. The colored aqueous solution of claim 1, wherein the color fades to clear within a predetermined period of time of from 1 to 20 minutes when the solution is applied as a spray or film to a surface.
17. The colored aqueous solution of claim 1, wherein the colored solution is impregnated onto a solid material.
18. The colored aqueous solution of claim 17, wherein the solid material is a fabric or mesh.
19. The colored aqueous solution of claim 17, wherein the solid material is a pre-packaged wipe.

20. The colored aqueous solution of claim 1, wherein the solution is part of a dispenser for wipes.

* * * * *

UNITED STATES PATENT AND TRADEMARK OFFICE
CERTIFICATE OF CORRECTION

| | | |
|---|---|---|
| PATENT NO. | : 10,329,520 B2 | Page 1 of 1 |
| APPLICATION NO. | : 15/668267 | |
| DATED | : June 25, 2019 | |
| INVENTOR(S) | : Jason Kang et al. | |

It is certified that error appears in the above-identified patent and that said Letters Patent is hereby corrected as shown below:

In the Specification

On Column 1, Line 16, add a government clause as follows:
--STATEMENT AS TO THE RIGHTS TO INVENTIONS MADE UNDER FEDERALLY SPONSORED RESEARCH AND DEVELOPMENT
This invention was made with government support under award AID-OAA-F-15-00026 awarded by the US Agency for International Development. The government has certain rights in the invention.--

Signed and Sealed this
Fifth Day of May, 2020

Andrei Iancu
*Director of the United States Patent and Trademark Office*